(12) United States Patent
Ahmed et al.

(10) Patent No.: US 11,197,910 B1
(45) Date of Patent: Dec. 14, 2021

(54) FUSION PROTEINS FOR THE DIAGNOSIS, PROPHYLAXIS AND TREATMENT OF INFECTIOUS DISEASES

(71) Applicant: Vitruviae LLC, Nutley, NJ (US)

(72) Inventors: Mahiuddin Ahmed, Verona, NJ (US); Sonia Sequeira, Verona, NJ (US)

(73) Assignee: VITRUVIAE LLC, Nutley, NJ (US)

( * ) Notice: Subject to any disclaimer, the term of this patent is extended or adjusted under 35 U.S.C. 154(b) by 0 days.

(21) Appl. No.: 16/997,639

(22) Filed: Aug. 19, 2020

(51) Int. Cl.
| | |
|---|---|
| A61K 38/16 | (2006.01) |
| C07K 14/76 | (2006.01) |
| C07K 14/735 | (2006.01) |
| A61K 39/02 | (2006.01) |
| A61K 39/00 | (2006.01) |
| A61K 39/12 | (2006.01) |
| A61K 39/002 | (2006.01) |
| A61K 47/68 | (2017.01) |

(52) U.S. Cl.
CPC .......... *A61K 38/16* (2013.01); *A61K 39/0002* (2013.01); *A61K 39/002* (2013.01); *A61K 39/02* (2013.01); *A61K 39/12* (2013.01); *A61K 47/68* (2017.08); *C07K 14/70535* (2013.01); *C07K 14/76* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 2004/0053366 | A1* | 3/2004 | Lo | C07K 14/5759 435/69.1 |
| 2005/0276756 | A1* | 12/2005 | Hoo | A61P 19/02 424/1.49 |
| 2006/0104975 | A1* | 5/2006 | Geijtenbeek | A61P 33/00 424/144.1 |
| 2009/0263378 | A1* | 10/2009 | Ravetch | A61P 17/06 424/130.1 |
| 2014/0294823 | A1 | 10/2014 | Moore et al. | |
| 2018/0371089 | A1 | 12/2018 | Wu et al. | |

FOREIGN PATENT DOCUMENTS

| | | |
|---|---|---|
| WO | 2008086006 A2 | 7/2008 |
| WO | 2010102251 A2 | 9/2010 |
| WO | 2016071004 A1 | 5/2016 |
| WO | 2017008169 A1 | 1/2017 |
| WO | 2017181139 A2 | 10/2017 |
| WO | 2017218707 A2 | 12/2017 |

OTHER PUBLICATIONS

Cummings et al., Chapter 31 C-type Lectins, from Essentials of Glycobiology, Varki A, Cummings RD, Esko JD, et al., editors.. 2nd edition. Cold Spring Harbor (NY): Cold Spring Harbor Laboratory Press; 2009, 15 pages.*
Dumet et al., MAbs. Nov.-Dec. 2019;11(8):1341-1350. doi: 10.1080/19420862.2019.1664365. Epub Sep. 26, 2019.*
Hsu et al., J Biol Chem. Dec. 11, 2009;284(50):34479-89. doi: 10.1074/jbc.M109.065961. Epub Oct. 16, 2009.*
Wong et al. "Anti-CD3:Anti-IL-2 Receptor Bispecific Monoclonal Antibody" In Journal of Immunology, 1993; 150: 1619-1628), 11 pages.
Ahmed et al. "In silica Driven Redesign of a Clinically Relevant Antibody for the Treatment of GD2 Positive Tumors", Available at: (PLOS ONE | www.plosone.org, May 1, 2013 | vol. 8 | Issue 5 | e63359, 9 Pages.
Cheng et al, "Structural design of disialoganglioside GD2 and CD3-bispecific antibodies to redirect T cells for tumor therapy" In International Journal of Cancer: 136, 476-486 (2015.), 11 pages.
"Tiziana Reports Positive Data from the Clinical Study of Nasal Administiation with Foralumab, its proprietary fully human anti-CD3 monoclonal antibody, in COVID-19 Patients in Brazil," Tiziana Life Sciences, Intrado GlobeNewswire, Feb. 2, 2021.

* cited by examiner

*Primary Examiner* — Michael Szperka
(74) *Attorney, Agent, or Firm* — Holzer Patel Drennan

(57) ABSTRACT

The present invention relates to the use of phosphotidylserine or pathogenic sugar targeted therapeutics for the management and treatment of microbial infections, including Zika, Dengue, West Nile, Ebola, H1N1, enteroviruses, Leishmaniasis, Malaria and Coronaviruses SARS-COV.

8 Claims, 3 Drawing Sheets
Specification includes a Sequence Listing.

TIM-1 and CTLD constructs with enhanced ADCC, ADCP and CDC

TIM1 and CTLD T cell Engagers

TIM1 and CTLD with Furin Inhibitor Payload Delivery

VIT-307    VIT-308    VIT-309

Furin Inhibitor

FUSION PROTEINS FOR THE DIAGNOSIS, PROPHYLAXIS AND TREATMENT OF INFECTIOUS DISEASES

The present invention relates to the use of phosphotidylserine or pathogenic sugar targeted therapeutics for the management and treatment of microbial infections, including Zika, Dengue, West Nile, Ebola, H1N1, *Mycobacterium leprae, Mycobacterium tuberculosis*, Enteroviruses, Leishmaniasis, Malaria and Coronaviruses SARS-CoV.

Provided are compositions related to novel, therapeutic proteins including T cell engagers, platforms with cytotoxic functions or conjugated to furin protease inhibitors, mono and multivalent molecules, drug conjugates and adjuvants, carriers and methods of administration, in particular subcutaneous, oral or nasal administration. This invention further relates to a companion diagnostic as a method of selection of subjects that may benefit from such therapies and a blood biomarker for rapid and easy monitoring of response of treatment.

TECHNICAL BACKGROUND

According to WHO, the Arboviruses Zika Virus (ZIKV), Chikungunya (CHIKV), Dengue (DENV), West Nile (WNV), as well as Ebola (EBLV) and SARS are relatively recent, life-threatening, rare diseases prone to pandemic spread that pose a high global public health risk (WHO report 2020).

There are no FDA approved therapies for these diseases. A live, recombinant vaccine consisting of the envelope glycoprotein of one of the Ebola strains, Zaire Ebolavirus (Ervebo, 2019) was recently approved by the FDA for adult use only, although the duration of protection is still not entirely known. Another recombinant vaccine consisting of the pre-M and E proteins for all 4 strains of Dengue (Dengvaxia, 2019) has also been approved.

ZIKV, WNV and DENV are flaviviruses (family Flaviviridae) primarily transmitted by mosquito vectors (i.e. arboviruses). According to Ramos da Silva 2016, Zika is a positive single stranded flaviviridae virus mainly transmitted by the *Aedes* mosquito and an increasing number of strains in two phylogenetic lineages (Asian and African) have been identified since its first isolation in Uganda in 1947 (Ramos da Silva 2016). According to WHO outbreaks in 2015-2017 resulted in more than 30,000 cases world wide (Worlds Health Organization Zika Epidemiology update July 2019, Website: www_who.int/emergencies/diseases/zika/zika-epidemiology-update-july-2019.pdf?ua=1, accessed 5 Aug. 2020).

According to Musso 2015, Zika is also spread through sexual contact (Musso 2015) and according to Rasmussen 2016, Zika is also spread from maternal to fetal blood (Rasmussen 2016).

An expanding spectrum of neurological sequelae has been reported. According to Rasmussen 2016 a particularly serious co-morbidity of Zika infection in pregnant women is severe congenital microcephaly to their progeny (Rasmussen 2016). According to Barbi 2018, in adults, Guillain-Barré syndrome (GBS), an auto-immune disease that destroys the myelin sheath and causes progressive ascending paralysis has been estimated to affect 1.23% of patients (Barbi 2018). Less frequently reported ZIKV neurological complications include encephalitis/meningoencephalitis, acute disseminated encephalomyelitis, myelitis, cerebrovascular complications, seizures and encephalopathy, sensory polyneuropathy and sensory neuropathy.

Primary hosts of ZIKV include human, monkey, and mosquito. According to Hou 2017 neural stem cells, fibroblasts, epithelial and blood cells are permissive to ZIKV infection (Hou 2017).

Dengue virus (DEGV) is a negative RNA strand flavivirus that causes the most prevalent arthropod-born viral disease in the world (1 million cases/year). DENV infection causes human diseases with a wide spectrum of clinical symptoms, ranging from asymptomatic infection or self-limited febrile illness named Dengue fever (DF) to life-threatening diseases including Dengue hemorrhagic fever (DHF) and Dengue shock syndrome (DSS). There are currently no vaccines or therapies for Dengue.

The patent application US2009175865A1 describes antibodies that are engineered by replacing one or more amino acids of a parent antibody with non cross-linked, highly reactive cysteine amino acids. Among other mutations, the patent application mentions A339C and S337C.

The patent application WO2015157595 describes conjugate compounds comprising antibodies and fragments thereof engineered with one or more reactive cysteine residues. Among other mutations, the patent application mentions K340C.

According to Wenwen Bi et al. (IgG Fc-binding mortif-conjugated HIV-1 fusion inhibitor exhibits improved potency and in vivo half-life: Potential application in combination with broad neutralizing antibodies, PLOS Pathogens, Dec. 5, 2019) a strategy have been developed to extend the in vivo half-life of a short HIV-1 fusion inhibitory peptide, CP24, by fusing it with the human IgG Fc-binding peptide (IBP).

SUMMARY OF THE INVENTION

Similarities in the way viruses bind to permissive human cells, are activated in the endosomal-lysosomal compartments and become infectious, offer insights towards a potential pan-therapeutic approach to their treatment.

Pathogen Sugars as a CD209 Therapeutic Target

According to Sirohi 2016 and Kostyuchenko 2016 a crystal structure of ZIKV has been described (Sirohi, 2016, Kostyuchenko, 2016). The virus particle has 180 copies of the structural proteins E (envelope) and M (membrane) on the surface of the membrane.

According to Sirohi and Kuhn 2017 and Li 2019 protein E is a ligand for attachment to host receptors that is involved in viral fusion with the host membrane (Sirohi and Kuhn 2017, Li, 2019). These proteins are highly glycosylated.

Host C-type lectin receptors that recognize specific glycans have been shown to bind pathogens and to play a role in host defense. Glucans, polysaccharide moieties derived from D-glucose and linked to surface proteins or lipids, are prominent constituents of the cell walls of fungi, plants, and mycobacteria. High-mannose containing structures (mannans) are expressed by many viruses, fungi, and bacteria, and fucose structures (fucans) are found on the surface of helminths and some bacteria (Geijtenbeek and Gringhuis, 2009; Robinson et al., 2006).

The myeloid, dendritic and macrophage cell specific C-type lectin receptor CD209 (also known as DC-SIGN), (Zelensky and Gready, 2005) is an important host cell receptor for entry of ZIKV (Perera Lecoin, 2013, Osorio and Sousa 2011), Influenza (Gillespie 2016), DENV (Cruz-Oliveira, 2015), WNV (Davis 2006), Ebola (Alvarez 2002), enterovirus (REN 2014), *Mycobacterium tuberculosis* (Tailleux 2003) and *Mycobacterium leprae* (Barreiro 2006) and SARS-COV2/COVID19 (Amraei 2020, Cai 2020, Jeffers 2004). The protozoan vector borne disease Leshmaniasis and Malaria are non-viral pathogens that may exploit CD209 for host entry (Colmenares 2002, Morenikeji 2020). CD209 binds to both mannan (high-mannose N-linked oligosaccharides) and fucan moieties that comprise viral signatures or "pathogen associated molecular patterns (PAMPs). The binding occurs within a compact protein region with a unique structural fold that became known as the "C-type carbohydrate recognition domain" or "C-type lectin domain (CTLD)" (Weis and Drick-Amer, 1996).

There is no cure for COVID-19, currently a worldwide pandemic, however the FDA has granted emergency use authorization to some treatments such as the antiviral Remdesivir, although their effectiveness against Covid-19 has yet to be demonstrated in large-scale, randomized clinical trials. Among approaches in early preclinical development are ACE2 decoy proteins to block viral attachment to host cells, and off-label use of dexamethasone to reduce inflammation in patients on ventilators but not patients with early stage symptoms. Thus, there is an urgent need for effective and safe means for treating and alleviating COVID-19 and related symptoms. Thus, there is an urgent need for a diagnostic that can precisely select patients that may benefit from a particular treatment.

Phosphatidylserine (PS) Lipids as a TIM1 Therapeutic Target

The outer virus membrane layer of several viruses is rich in phospholipid phosphatidylserine (PS) whereas in the host cell membrane, PS is normally restricted to the inner membrane layer.

According to Freeman 2010 the T-cell immunoglobulin and mucin domain 1 (TIM-1) host receptor, which is expressed in the brain, gastrointestinal tract, liver and gallbladder, kidney, testis and lymphoid tissue, recognizes with high specificity exposed PS in dying, apoptotic cells and triggers their phagocytosis by the immune system (Freeman 2010). TIM-1, an important susceptibility gene for asthma and allergy, is preferentially expressed on T-helper 2 (Th2) cells and functions as a potent co-stimulatory molecule for T-cell activation.

It has been shown that TIM1 is an independent receptor for highly divergent viruses (Jemielity, 2013), including Zika (Lee 2018), Ebola (Brunton 2019), Dengue (Chu 2019, Amara 2015), West Nile (Richard 2015), Hepatitis A and possibly Malaria (Nuchnoi 2020). TIM1 (also known as HAVCR1) is a type I transmembrane glycoprotein that contains an extracellular domain composed of an N-terminal immunoglobulin variable (IgV)-like domain followed by a glycosylated mucin domain, a single transmembrane domain, and a short cytoplasmic tail with tyrosine phosphorylation motifs. The binding of TIM-1 with PS on apoptotic cells through its metal ion-dependent ligand binding site (MILIBS) within IgV domain promotes apoptotic clearance. TIM1 is the most well known PS receptor although other PS receptors have been described to a lesser extent such as Tyro3, Axl and Mer of the TAM family of proteins.

Furin Protease Inhibition as a Therapeutic Strategy

Furin cleavage sites are present in entry proteins of Zika, Dengue, COVID-19 (Coutard 2020), Ebola, HIV, and Hepatitis B viruses among others (Braun 2019).

Decanoyl-Arg-Val-Lys-Arg-chloromethylketone (dec-RVKR-cmk) comprising SEQ ID NO. 81 and hexa-D-arginine (D6R) are small synthetic furin inhibitors that have been used to show reduction of viral infectivity in vitro (Owczarek, 2019, Imran 2019, Remacle 2010, Couture 2015). CMK is more effective than D6R in the reduction of Hepatitis replication by inhibiting furin-mediated processing of the hepatitis B e-antigen (HBeAg) precursor into mature HBeAg. Dec-RVKR-cmk is a small, synthetic, irreversible, and cell-permeable competitive inhibitor of all proprotein convertases (PC1, PC2, PC4, PACE 4, PC5, PC7, and furin). CMK is reported to inhibit furin-mediated cleavage and fusion activity of viral glycoproteins, and acts as an antiviral agent against different viruses, including human immunodeficiency virus, Chikungunya virus, chronic hepatitis B virus, influenza A, Ebola virus infection and papilloma virus. Smith et al. and Steinmetzer et al. also patented a peptidomimetic furin inhibitor by modifying the C-terminal of dec-RVKR-cmk with decarboxylated arginine mimetics, resulting in highly potent furin inhibitors (Couture 2015).

Wide-range furin/proprotein inhibitors are thought to have minimal off-pathogen, on-target effects in the host given that proprotein convertases are highly redundant, as shown by furin knockout mice.

CMK has been shown to have anti-flavivirus activity at non-cytotoxic concentration (Imran 2019).

Zika virus contains 3 structural (capsid-pC, envelope-pE and membrane-prM) and 7 non-structural (NS) proteins (NS1, NS2A, NS2B, NS3, NS4A, NS4B and NS5). Zika virus replication occurs in the permissive host cell after internalization via clathrin-mediated ph dependent endocytosis and maturation of viral proteins in the lysosomal compartment (Owczarek, 2019). In the lysosome, furin or furin-like proteases cleave viral surface glycoprotein prM into its active form destabilizing the viral membrane and promoting release of the viral RNA for replication in mitochondria and endoplasmatic reticulum.

There is no vaccine for ZIKV although there are investigational agents in clinical development.

It has been shown that furin inhibition causes the immature virion to be transported to late compartments where it undergoes proteolytic degradation. The degradation products are ejected from the cell via slow recycling vesicles (Owczarek, 2019).

Similar to ZIKV, DENV binding of viral protein E with cellular receptors allows viral particles to internalize into the permissible cell via the chlathrin mediated endocytosis pathway. To release the viral RNA genome, DENV virions undergo an acid-induced conformational change and membrane fusion. Newly synthesized viral proteins generated near the endoplasmic reticulum (ER) promote replication of the viral RNA genome, induction of membrane rearrangement, and assembly of new viral particles. To facilitate the process of DENV replication, DENV not only interacts with various cellular components, but also triggers various host responses, such as autophagy.

T-Cell Mediated Therapy

CD3 is a protein complex and T cell co-receptor that is involved in activating T cells. CD3 is selectively expressed on T cells in blood, bone marrow and lymphoid tissues, but not on other normal tissues and with no cross reactivity to other animals except for chimpanzee.

Recently, human CD3 transgenic mice have been engineered, facilitating the study of anti-CD3 immunotherapies.

Anti-CD3 based therapies such as muromomab-CD3 (Janssen, Orthoclone, OKT3) have been extensively studied in humans both systemically and orally to block reactive T cells and ameliorate ulcerative cholitis and metabolic syndrome (da Cunha 2011, Ilan 2010-NCT01287195, NCT01205087). Anti-CD3 bispecific antibody platforms that bridge tumors and engage T cells such as blinatumomab and catumaxomab have been approved for the treatment of cancer and several others CD3 bispecifics are in clinical development (Suurs, 2019).

According to an aspect, the invention concerns a fusion construct comprising an Ig-Fc domain or other protein scaffold, such as albumin, and
   a. a peptide, protein or antibody fragment binding to phosphatidylserine and/or
   b. a peptide or protein binding to and/or recognizing a PAMP expressed by a microbe.

PAMP refers to Pathogen-associated molecular pattern: conserved molecular structures produced by microbial pathogens, but not by the host organism that are recognized by the host innate immune system.

According to another aspect, the invention concerns a fusion construct comprising an IgG-Fc domain or other protein scaffold and
   a. a recombinant human TIM1 fragment and/or
   b. a recombinant human CD209 fragment.

According to another aspect, the invention concerns a fusion construct comprising an IgG-Fc domain or other protein scaffold and
   a. a recombinant human TIM1 fragment and/or
   b. a recombinant human CD209 fragment
and wherein said fusion construct provides enhanced ADCC, ADCP and/or CDC.

ADCC may be defined as Antibody-Dependent Cellular Cytotoxicity. ADCP may be defined as Antibody-Dependent Cellular Phagocytosis. CDC may be defined as Complement-dependent cytotoxicity.

According to another aspect, the invention concerns a fusion construct comprising an IgG-Fc domain or other protein scaffold and
   a. a recombinant human TIM1 fragment and/or
   b. a recombinant human CD209 fragment
and wherein said fusion construct additionally comprises the CDR regions according to SEQ ID No.: 54-59.

According to another aspect, the invention concerns a fusion construct comprising an IgG-Fc domain or other protein scaffold and
   a. a recombinant human TIM1 fragment and/or
   b. a recombinant human CD209 fragment
and wherein said fusion construct further comprises a Furin inhibitor.

Preferably the Furin inhibitor is selected among chloromethylketone and D-arginine derivatives such as hexa-D-arginine and dec-RVKR-cmk (comprising SEQ ID NO. 81).

The linker and spacers may be conjugated to furin, see Table 7.

According to another aspect, the invention concerns a fusion construct, wherein said fusion construct is an IgG3 construct, and wherein said IgG3 construct comprises a hinge region, wherein said hinge region has been modified.

According to another aspect, the invention concerns a fusion construct, a fusion protein or an antibody comprising the constant region(s) of IgG3 and a hinge, wherein said hinge preferably is selected among an IgG1 or IgG4 hinge.

According to another aspect, the invention concerns IgG3 homodimer comprising a hinge region, wherein said hinge region comprises a sequence selected among SEQ ID No.: 6, 8 and 68.

According to another aspect, the invention concerns IgG3 heterodimer comprising a hinge region, wherein said hinge region comprises a sequence selected among SEQ ID No.: 6, 8 and 68.

According to another aspect, the invention concerns IgG3, wherein said IgG3 comprises a mutation at position 405 and/or position 409. According to another aspect, the invention concerns IgM heterodimers obtainable by changing the charge pairs of the CH2 and/or CH4 domains.

According to another aspect, the invention concerns IgM heterodimers, comprising one or more of the mutations of Table 8.

According to another aspect, the invention concerns a fusion construct, wherein said fusion construct comprises an IgG3 homodimer, an IgG3 heterodimer and/or an IgM heterodimer according to the invention.

According to another aspect, the invention concerns use of a fusion construct according to the invention for the treatment of an infection.

According to another aspect, the invention concerns use, wherein said infections are selected among viral, bacterial and protozoan infections.

According to another aspect, the invention concerns use, wherein the treatment comprising administration of the fusion construct with an administration form selected among subcutaneous, intradermal, intramuscular, oral and nasal.

According to another aspect, the invention concerns use of IgG4 or a part of IgG4 for payload delivery, wherein said IgG4 has been modified to comprise no Fc or wherein the activity of the Fc of said IgG4 has been nullified or diminished by one or more mutations.

According to another aspect, the invention concerns a vaccine comprising a fusion construct according to the invention.

According to another aspect, the invention concerns a vaccine comprising a mannan, a high-mannose containing structure, a fucan and/or a phospholipid phosphatidylserine (PS).

According to another aspect, the invention concerns a composition comprising a fusion construct according to the invention, optionally comprising one or more excipients such as diluents, binders or carriers.

According to another aspect, the invention concerns a method of treating and/or preventing an infection in a subject, comprising a step of administration of a fusion construct and/or a vaccine and/or a composition according to the invention.

According to another aspect, the invention concerns a method of screening and/or monitoring progression of a disease in a subject, wherein said method comprises the following steps:
   i. Providing a blood sample from said subject.
   ii. Contacting said blood sample with a fusion construct according to the invention.

According to another aspect, the invention concerns an isolated nucleic acid molecule encoding a fusion construct according to the invention.

According to another aspect, the invention concerns a recombinant vector comprising the nucleic acid molecule of the invention.

According to another aspect, the invention concerns a host cell comprising the recombinant vector of the invention.

According to another aspect, the invention concerns a method for the production of a fusion construct according to the invention comprising a step of culturing the host cell according to the invention in a culture medium under conditions allowing the expression of the fusion construct and separating the fusion construct from the culture medium.

DETAILED DISCLOSURE

According to an embodiment, the invention concerns a fusion construct comprising an Ig-Fc domain or other protein scaffold, such as albumin, and a. a peptide, protein or antibody fragment binding to phosphatidylserine and/or
b. a peptide or protein binding to and/or recognizing a PAMP expressed by a microbe.

PAMP refers to Pathogen-associated molecular pattern: conserved molecular structures produced by microbial pathogens, but not by the host organism that are recognized by the host innate immune system.

According to an embodiment, the invention concerns a fusion construct comprising an IgG-Fc domain or other protein scaffold and
a. a recombinant human TIM1 fragment and/or
b. a recombinant human CD209 fragment.

According to an embodiment, the invention concerns a fusion construct comprising an IgG-Fc domain or other protein scaffold and
a. a recombinant human TIM1 fragment and/or
b. a recombinant human CD209 fragment
and wherein said fusion construct provides enhanced ADCC, ADCP and/or CDC.

ADCC may be defined as Antibody-Dependent Cellular Cytotoxicity. ADCP may be defined as Antibody-Dependent Cellular Phagocytosis. CDC may be defined as Complement-dependent cytotoxicity.

According to an embodiment, the invention concerns a fusion construct comprising an IgG-Fc domain or other protein scaffold and
a. a recombinant human TIM1 fragment and/or
b. a recombinant human CD209 fragment
and wherein said fusion construct additionally comprises the CDR regions according to SEQ ID No.: 54-59.

According to an embodiment, the invention concerns a fusion construct comprising an IgG-Fc domain or other protein scaffold and
a. a recombinant human TIM1 fragment and/or
b. a recombinant human CD209 fragment
and wherein said fusion construct further comprises a Furin inhibitor.

Preferably the Furin inhibitor is selected among chloromethylketone and D-arginine derivatives such as hexa-D-arginine and dec-RVKR-cmk (comprising SEQ ID NO. 81).

The linker and spacers may be conjugated to furin, see Table 7.

According to an embodiment, the invention concerns the fusion construct, wherein said peptide, protein or antibody fragment is capable of binding to and/or stimulating an immune cell.

According to an embodiment, the invention concerns the fusion construct, wherein said TIM1 fragment has a sequence length selected from the group consisting of 40-200 amino acid residues, 50-180 amino acid residues, 60-160 amino acid residues, 70-140 amino acid residues, 80-130 amino acid residues, 90-120 amino acid residues, 100-120 amino acid residues and 100-110 amino acid residues.

According to an embodiment, the invention concerns the fusion construct, wherein said CD209 fragment has a sequence length selected from the group consisting of 40-200 amino acid residues, 40-190 amino acid residues, 50-180 amino acid residues, 60-170 amino acid residues, 70-160 amino acid residues, 80-150 amino acid residues, 90-150 amino acid residues, 100-150 amino acid residues, 110-150 amino acid residues, 120-150 amino acid residues and 130-140 amino acid residues.

According to an embodiment, the invention concerns the fusion construct, wherein said TIM1 and/or CD209 fragment has a sequence homology of at least 70%, alternatively 75%, alternatively 80%, alternatively 85%, alternatively 90%, alternatively 95% to wildtype TIM1 or CD209.

According to an embodiment, the invention concerns the fusion construct, wherein said TIM1 and/or CD209 fragment has intact TIM1 and/or CD209 function.

According to an embodiment, the invention concerns the fusion construct, wherein said IgG-Fc domain is an IgG3-Fc domain.

According to an embodiment, the invention concerns the fusion construct, comprising additionally at least one of the following:
a) An IgG3, wherein the hinge sequence has been replaced, preferably with an IgG4 hinge sequence;
b) CDR regions according to SEQ ID No.: 54-59 and/or
c) A furin inhibitor.

According to an embodiment, the invention concerns the fusion construct, wherein said fusion construct comprises a sequence according to SEQ ID No.: 1 and/or SEQ ID No.: 2.

According to an embodiment, the invention concerns the fusion construct, wherein said fusion construct comprises a sequence according to SEQ ID No.: 3 and/or SEQ ID No.: 4.

According to an embodiment, the invention concerns the fusion construct, wherein said fusion construct comprises at least 1, at least 2, at least 3, at least 4, at least 5, at least 6, at least 7 or preferably at least 8 disulfide bonds.

According to an embodiment, the invention concerns the fusion construct, wherein said fusion construct is capable of binding to a target, and wherein said target is a mannan, a high-mannose containing structure, a fucan, a phospholipid phosphatidylserine and/or CD3.

According to an embodiment, the invention concerns the fusion construct, wherein said fusion construct comprises:
a. A first chain comprising
  i. a sequence according to SEQ ID No.: 1 or SEQ ID No.: 2 and
  ii. a sequence according to SEQ ID No.: 9 or a sequence according to SEQ ID No.: 43, and
b. A second chain comprising
  iii. a sequence according to SEQ ID No.: 1 or SEQ ID No.: 2, and
  iv. a sequence according to SEQ ID No.: 9 or a sequence according to SEQ ID No.: 43.

According to an embodiment, the invention concerns the fusion construct, wherein said fusion construct comprises:
a. A first chain comprising
  i. a sequence according to SEQ ID No.: 3 or SEQ ID No.: 4, and
  ii. a sequence according to SEQ ID No.: 9 or a sequence according to SEQ ID No.: 43, and
b. A second chain comprising
  iii. a sequence according to SEQ ID SEQ ID No.: 3 or SEQ ID No.: 4, and
  iv. a sequence according to SEQ ID No.: 9 or a sequence according to SEQ ID No.: 43.

According to an embodiment, the invention concerns the fusion construct, wherein said fusion construct comprises:
a. A first chain comprising
  i. a sequence according to SEQ ID No.: 1 or SEQ ID No.: 2, and
  ii. a sequence according to SEQ ID No.: 11 or a sequence according to SEQ ID No.: 45, and
b. A second chain comprising
  iii. a sequence according to SEQ ID No.: 3 or SEQ ID No.: 4, and iv. a sequence according to SEQ ID No.: 13 or a sequence according to SEQ ID No.: 47.

According to an embodiment, the invention concerns the fusion construct, wherein said fusion construct comprises:
a. A first chain comprising
  i. a sequence according to SEQ ID No.: 1 or SEQ ID No.: 2, and
  ii. a sequence according to SEQ ID No.: 14 or 15 or 66, and
b. A second chain comprising
  iii. a sequence according to SEQ ID No.: 1 or SEQ ID No.: 2, and
  iv. a sequence according to SEQ ID No.: 16 or 17 or 67, and
  v. a linker sequence, preferably according to SEQ ID No.: 41, and
  vi. a sequence according to any of the sequences selected among SEQ ID No.: 18-35.

According to an embodiment, the invention concerns the fusion construct, wherein said fusion construct comprises:
a. A first chain comprising
  i. a sequence according to SEQ ID No.: 3 or SEQ ID No.: 4, and
  ii. a sequence according to SEQ ID No.: 14 or 15 or 66, and
b. A second chain comprising
  iii. a sequence according to SEQ ID No.: 3 and/or SEQ ID No.: 4, and
  iv. a sequence according to SEQ ID No.: 16 or 17 or 67, and
  v. a linker sequence preferably according to SEQ ID No.: 41, and
  vi. a sequence according to any of the sequences selected among SEQ ID No.: 18-35.

According to an embodiment, the invention concerns the fusion construct, wherein said fusion construct comprises:
a. A first chain comprising
  i. a sequence according to SEQ ID No.: 1 or SEQ ID No.: 2, and
  ii. a sequence according to SEQ ID No.: 14 or 15 or 66, and
b. A second chain comprising
  iii. a sequence according to SEQ ID No.: 3 or SEQ ID No.: 4, and
  iv. a sequence according to SEQ ID No.: 16 or 17 or 67, and
  v. a linker sequence preferably according to SEQ ID No.: 41, and
  vi. a sequence according to any of the sequences selected among SEQ ID No.: 18-35.

According to an embodiment, the invention concerns the fusion construct, wherein said fusion construct comprises
a. A first chain comprising
  i. a sequence according to SEQ ID No.: 1 or SEQ ID No.: 2, and
  ii. a sequence according to SEQ ID No.: 16 or 17 or 67, and
  iii. a linker sequence preferably according to SEQ ID No.: 41, and
  iv. a sequence according to any of the sequences selected among SEQ ID No.: 18-35, and
b. A second chain comprising
  v. a sequence according to SEQ ID No.: 3 or SEQ ID No.: 4,
  vi. a linker sequence preferably according to SEQ ID No.: 41, and
  vii. a sequence according to SEQ ID No.: 14 or 15 or 66.

According to an embodiment, the invention concerns the fusion construct, wherein said fusion construct comprises a linker.

According to an embodiment, the invention concerns the fusion construct, wherein said linker is selected among a (GGGGS)3 linker (SEQ ID NO. 41), a (GGGGS)4 linker (SEQ ID NO. 70), a (GGGGS)5 linker (SEQ ID NO. 71) and a (GGGGS)6 linker (SEQ ID NO. 72).

A (GGGGS) linker may be defined as a Gly-Gly-Gly-Gly-Ser linker (SEQ ID NO. 69).

According to an embodiment, the invention concerns the fusion construct, wherein said fusion construct comprises at least one free cysteine residue, at least two free cysteine residues, at least three free cysteine residues, at least four free cysteine residues, at least five free cysteine residues or preferably at least six free cysteine residues.

According to an embodiment, the invention concerns the fusion construct, wherein said free cysteine allows interaction with a drug and/or a payload.

According to an embodiment, the invention concerns the fusion construct, wherein said payload is a furin inhibitor.

According to an embodiment, the invention concerns the fusion construct, wherein said fusion construct comprises a A339C mutation, a S337C mutation and/or a K340C mutation.

According to an embodiment, the invention concerns the fusion construct, wherein said fusion construct comprises a sequence selected among any of the sequences SEQ ID No.: 36, 37, SEQ ID No.: 38, 39, 40, 42, 44 or 46.

According to an embodiment, the invention concerns the fusion construct, wherein said fusion construct is an IgG1, IgG2, IgG3 or an IgG4.

According to an embodiment, the invention concerns the fusion construct, wherein said fusion construct is an IgG, IgM, IgA, IgD or an IgE.

According to an embodiment, the invention concerns the fusion construct, wherein said fusion construct comprises a null fc.

According to an embodiment, the invention concerns the fusion construct, wherein said null fc comprises an Ala substitution at position 234 and/or Ala substitution at 235, and/or N297A, and/or a K322A mutation.

According to an embodiment, the invention concerns the fusion construct, wherein said fusion construct comprises a heterodimerization domain.

According to an embodiment, the invention concerns the fusion construct, wherein said heterodimerization domain comprises a sequence according to SEQ ID No.: 48, 49 or 50.

According to an embodiment, the invention concerns the fusion construct, wherein said fusion construct comprises a heterodimerization mutation.

According to an embodiment, the invention concerns the fusion construct, wherein said heterodimerization mutation is an F405L and/or K409R mutation.

According to an embodiment, the invention concerns the fusion construct, wherein said fusion construct comprises:
a. A first chain comprising
  i. a sequence according to SEQ ID No.: 1 or SEQ ID No.: 2, and
  ii. a sequence according to SEQ ID No.: 38, and
b. A second chain comprising
  iii. a sequence according to SEQ ID No.: 1 or SEQ ID No.: 2, and
  iv. a sequence according to SEQ ID No.: 38.

According to an embodiment, the invention concerns the fusion construct, wherein said fusion construct comprises:

a. A first chain comprising
   i. a sequence according to SEQ ID No.: 3 or SEQ ID No.: 4, and
   ii. a sequence according to SEQ ID No.: 38, and
b. A second chain comprising
   iii. a sequence according to SEQ ID No.: 3 or SEQ ID No.: 4, and
   iv. a sequence according to SEQ ID No.: 38.

According to an embodiment, the invention concerns the fusion construct, wherein said fusion construct comprises:
a. A first chain comprising
   i. a sequence according to SEQ ID No.: 1 or SEQ ID No.: 2, and
   ii. a sequence according to SEQ ID No.: 38, and
b. A second chain comprising
   iii. a sequence according to SEQ ID No.: 3 or SEQ ID No.: 4, and
   iv. a sequence according to SEQ ID No.: 40.

According to an embodiment, the invention concerns the fusion construct, wherein said fusion construct comprises:
a. A first chain comprising
   i. a sequence according to SEQ ID No.: 1 or SEQ ID No.: 2, and
   ii. a linker sequence according to SEQ ID No.: 41, and
   iii. a sequence according to SEQ ID No.: 65
b. A second chain comprising
   v. a sequence according to SEQ ID No.: 1 or SEQ ID No.: 2, and
   vi. a linker sequence according to SEQ ID No.: 41, and
   vii. a sequence according to SEQ ID No.: 65

According to an embodiment, the invention concerns the fusion construct, wherein said fusion construct comprises:
a. A first chain comprising
   i. a sequence according to SEQ ID No.: 3 or SEQ ID No.: 4, and
   ii. a linker sequence according to SEQ ID No.: 41, and
   iii. a sequence according to SEQ ID No.: 65
b. A second chain comprising
   iv. a sequence according to SEQ ID No.: 3 or SEQ ID No.: 4, and
   v. a linker sequence according to SEQ ID No.: 41, and
   vi. a sequence according to SEQ ID No.: 65

According to an embodiment, the invention concerns the fusion construct, wherein said fusion construct comprises:
a. A first chain comprising
   i. a sequence according to SEQ ID No.: 1 or SEQ ID No.: 2, and
   ii. a linker sequence according to SEQ ID No.: 41, and
   iii. a sequence according to SEQ ID No.: 65, wherein said sequence ID No.: 65 comprises one or more of the mutations of table 8
b. A second chain comprising
   iv. a sequence according to SEQ ID No.: 3 or SEQ ID No.: 4, and
   v. a linker sequence according to SEQ ID No.: 41, and
   vi. a sequence according to SEQ ID No.: 65, wherein said sequence ID No.: 65 comprises one or more of the mutations of table 8.

According to an embodiment, the invention concerns the fusion construct, wherein the ratio of fusion construct to said drug and/or payload is selected among 1, 2, 3, 4, 5, 6, 7, 8, 9 or 10.

According to an embodiment, the invention concerns the fusion construct, wherein said fusion construct comprises a kappa light chain according to SEQ ID No.: 51 or a lambda light chain according to SEQ ID No.: 52 or 53.

According to an embodiment, the invention concerns a fusion construct, wherein said fusion construct is an IgG3 construct, and wherein said IgG3 construct comprises a hinge region, wherein said hinge region has been modified.

According to an embodiment, the invention concerns the fusion construct, wherein said hinge region comprises a sequence having a total of at least 10% identity, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identity to the sequence according to SEQ ID No.: 6 or SEQ ID No.: 8.

According to an embodiment, the invention concerns the fusion construct, wherein said fusion construct comprises the sequence according to SEQ ID No.: 5, 7, 9, 10, 11, 12 and/or 13.

According to an embodiment, the invention concerns the fusion construct, wherein said hinge region comprises at least one free cysteine residue, at least two free cysteine residues or preferably at least three free cysteine residues.

According to an embodiment, the invention concerns the fusion construct, wherein said hinge region comprises a S228P mutation.

According to an embodiment, the invention concerns the fusion construct, wherein said hinge region comprises a sequence according to SEQ ID No.: 6 and/or SEQ ID No.: 8 and/or SEQ ID No.: 68.

According to an embodiment, the invention concerns the fusion construct, wherein said fusion construct is used to detect phosphatidylserine.

According to an embodiment, the invention concerns the fusion construct, wherein said fusion construct is used to detect phosphatidylserine in the blood of a subject.

According to an embodiment, the invention concerns the fusion construct, wherein said fusion construct comprises a sequence according to SEQ ID No.: 1, and/or a sequence according to SEQ ID No.: 2.

According to an embodiment, the invention concerns the fusion construct, wherein said fusion construct is used to detect C-type lectin binding mannan or fucan moieties.

According to an embodiment, the invention concerns the fusion construct, wherein said fusion construct is used to detect C-type lectin binding mannan or fucan moieties in the blood of a subject.

According to an embodiment, the invention concerns the fusion construct, wherein said fusion construct comprises a sequence according to SEQ ID No.: 3 and/or a sequence according to SEQ ID No.: 4.

According to an embodiment, the invention concerns a fusion construct, a fusion protein or an antibody comprising the constant region(s) of IgG3 and a hinge, wherein said hinge preferably is selected among an IgG1 or IgG4 hinge.

According to an embodiment, the invention concerns the fusion construct, fusion protein or antibody, comprising one or more heterodimerization mutations.

According to an embodiment, the invention concerns the fusion construct, fusion protein or antibody, comprising heterodimerization mutations involve positions 405 and/or 409 (EU numbering).

According to an embodiment, the invention concerns IgG3 homodimer comprising a hinge region, wherein said hinge region comprises a sequence selected among SEQ ID No.: 6, 8 and 68.

According to an embodiment, the invention concerns IgG3 heterodimer comprising a hinge region, wherein said hinge region comprises a sequence selected among SEQ ID No.: 6, 8 and 68.

According to an embodiment, the invention concerns IgG3, wherein said IgG3 comprises a mutation at position 405 and/or position 409.

According to an embodiment, the invention concerns IgM heterodimers obtainable by changing the charge pairs of the CH2 and/or CH4 domains.

According to an embodiment, the invention concerns IgM heterodimers, comprising one or more of the mutations of Table 8.

According to an embodiment, the invention concerns the IgM, wherein said IgM comprises a sequence according to SEQ ID No.: 64 and/or 65.

According to an embodiment, the invention concerns a fusion construct, wherein said fusion construct comprises an IgG3 homodimer, an IgG3 heterodimer and/or an IgM heterodimer according to the invention.

According to an embodiment, the invention concerns the fusion construct, wherein said fusion construct is for use in the treatment of an infection.

According to an embodiment, the invention concerns the fusion construct, wherein said infection is an infection caused by a virus, a parasite, a bacteria, a fungi or a protozoan.

According to an embodiment, the invention concerns the fusion construct, wherein said virus is selected among an arborvirus, Zika virus, Dengue virus, West Nile virus, Ebola virus, influenza virus, influenza virus H1N1, Chikungunya virus, enterovirus and Coronaviruses SARS-COV.

According to an embodiment, the invention concerns the fusion construct, wherein said bacteria is selected among *Mycobacterium tuberculosis* and *Mycobacterium leprae*.

According to an embodiment, the invention concerns the fusion construct, wherein said parasite is selected among Leishmaniasis and Malaria.

According to an embodiment, the invention concerns use of a fusion construct according to the invention for the treatment of an infection.

According to an embodiment, the invention concerns use, wherein said infections are selected among viral, bacterial and protozoan infections.

According to an embodiment, the invention concerns use, wherein the treatment comprising administration of the fusion construct with an administration form selected among subcutaneous, intradermal, intramuscular, oral and nasal.

According to an embodiment, the invention concerns use of IgG4 or a part of IgG4 for payload delivery, wherein said IgG4 has been modified to comprise no Fc or wherein the activity of the Fc of said IgG4 has been nullified or diminished by one or more mutations.

According to an embodiment, the invention concerns the use, wherein said IgG4 comprises one or more heterodimerization mutations.

According to an embodiment, the invention concerns the use, wherein said IgG4 comprises one or more Cys mutations, preferably thereby allowing site specific conjugation.

According to an embodiment, the invention concerns the use, wherein said IgG4 comprises a Cys at position 339 (EU numbering).

According to an embodiment, the invention concerns a vaccine comprising a fusion construct according to the invention.

According to an embodiment, the invention concerns a vaccine comprising a mannan, a high-mannose containing structure, a fucan and/or a phospholipid phosphatidylserine (PS).

According to an embodiment, the invention concerns the vaccine further comprising β-glucan.

β-glucan adjuvant to potentiate immune response.

According to an embodiment, the invention concerns the vaccine, for the prevention and/or treatment of an infection.

According to an embodiment, the invention concerns the vaccine, wherein said infection is coursed by a virus, a parasite, a bacteria, a fungi or a protozoan.

According to an embodiment, the invention concerns the fusion construct and/or vaccine, wherein said fusion construct and/or vaccine allows administration through a route selected among subcutaneous administration, intradermal administration, intramuscular administration, oral administration and/or nasal administration.

According to an embodiment, the invention concerns a composition comprising a fusion construct according to the invention, optionally comprising one or more excipients such as diluents, binders or carriers.

According to an embodiment, the invention concerns a method of treating and/or preventing an infection in a subject, comprising a step of administration of a fusion construct and/or a vaccine and/or a composition to the invention.

According to an embodiment, the invention concerns a method of screening and/or monitoring progression of a disease in a subject, wherein said method comprises the following steps:

i. Providing a blood sample from said subject.
ii. Contacting said blood sample with a fusion construct according to the invention.

According to an embodiment, the invention concerns an isolated nucleic acid molecule encoding a fusion construct according to the invention.

According to an embodiment, the invention concerns a recombinant vector comprising the nucleic acid molecule according to the invention.

According to an embodiment, the invention concerns a host cell comprising the recombinant vector according to the invention.

According to an embodiment, the invention concerns a method for the production of a fusion construct according to the invention comprising a step of culturing the host cell according to the invention in a culture medium under conditions allowing the expression of the fusion construct and separating the fusion construct from the culture medium.

Additional embodiments of the invention are described below.

According to an embodiment, the invention concerns a fusion construct, wherein said fusion construct comprises a hinge region, wherein said hinge region comprises any of the sequences as described below:

| Construct | Hinge region sequence | |
|---|---|---|
| IgG1 | -KS--CDKTHT----------CPPCPAP | (SEQ ID NO. 73) |
| IgG2 | -K---------------CCVECPPCPAP | (SEQ ID NO. 74) |
| IgG3 | LKTPLGDITHIPEPKSCDTPPPCPRCPAP | (SEQ ID NO. 6) |

-continued

| Construct | Hinge region sequence | |
|---|---|---|
| IgG4 | SKY--G-------------PPCPSCPAP | (SEQ ID NO. 75) |
| V-IGG2, -A, -B | -KD-------------KTHTCPPCPAP | (SEQ ID NO. 76) |
| V-IGG2-C, -D, -E | -K---------------YGPPCPPCPAP | (SEQ ID NO. 77) |
| V-IGG3, -A, -B | SKY--G-------------PPCPPCPAP | (SEQ ID NO. 78) |
| V-IGG3-C, -D, -E | LKT--GDTTHT-----------CPRCPAP | (SEQ ID NO. 79) |
| V-IGG4-A, -B | SKY--G-------------PPCPPCPAP | (SEQ ID NO. 80) |

According to an embodiment, the invention concerns a fusion construct, wherein said fusion construct comprises an Fc heterodimerization sequence at residue 405-409, wherein said Fc heterodimerization sequence comprises a sequence according to SEQ ID No.: 48, 49 or 50. IgG Fc heterodimerization sequences (residues 405-409)

| Construct | Sequence | |
|---|---|---|
| IgG2 | FLYSK | SEQ ID No.: 48 |
| V-IGG2/-C | FLYSK | SEQ ID No.: 48 |
| V-IGG2-A/-D | FLYSR | SEQ ID No.: 49 |
| V-IGG2-B/-E | LLYSK | SEQ ID No.: 50 |
| IgG3 | FLYSK | SEQ ID No.: 48 |
| V-IGG3/-C | FLYSK | SEQ ID No.: 48 |
| V-IGG3-A/-D | FLYSR | SEQ ID No.: 49 |
| V-IGG3-B/-E | LLYSK | SEQ ID No.: 50 |
| IgG4 | FLYSR | SEQ ID No.: 49 |
| V-IGG4-A | FLYSR | SEQ ID No.: 49 |
| V-IGG4-B | LLYSK | SEQ ID No.: 50 |

Immunoglobulins are glycoproteins composed of one or more units, each containing four polypeptide chains: two identical heavy chains (HCs) and two identical light chains (LCs). The amino terminal ends of the polypeptide chains show considerable variation in amino acid composition and are referred to as the variable (V) regions to distinguish them from the relatively constant (C) regions. Each light chain consists of one variable domain, VL, and one constant domain, CL. The heavy chains consist of a variable domain, VH, and three constant domains CH1, CH2 and CH3. Heavy and light chains are held together by a combination of non-covalent interactions and covalent interchain disulfide bonds, forming a bilaterally symmetric structure. The V regions of H and L chains comprise the antigen-binding sites of the immunoglobulin (Ig) molecules. Each Ig monomer contains two antigen-binding sites and is said to be bivalent.

The Fab contains one complete L chain in its entirety and the V and CH1 portion of one H chain. The Fab can be further divided into a variable fragment (Fv) composed of the VH and VL domains, and a constant fragment (Fb) composed of the CL and CH1 domains.

The H chain constant domain is generally defined as CH1-CH2-CH3 (IgG, IgA, IgD) with an additional domain (CH4) for IgM and IgE. As described above, the CH1 domain is located within the F(ab) region whereas the remaining CH domains (CH2-CH3 or CH2-CH4) comprise the Fc fragment. This Fc fragment defines the isotype and subclass of the immunoglobulin.

CH3 domain: The terms CH3 domain and CH3 region are used interchangeably herein.

CH1 domain: The terms CH1 domain and CH1 region are used interchangeably herein.

Hinge region: The hinge region is the area of the heavy chains between the first and second C region domains and is held together by disulfide bonds. A hinge region typically comprises between 10 and 30 amino acid residues.

Linker: A linker might be a peptide linker or a non-peptide linker. An example of a peptide linker is a Gly/Ser peptide linker comprising a five amino acid residue unit, GGGGS (SEQ ID NO:71), that can be repeated a suitable amount of times. A linker might be a naturally occurring linker or a synthetically produced linker. A linker might occur naturally in a molecule or might be synthetically added to a molecule.

Antibody fragment: As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen.

Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen-binding fragment of an antibody may be produced by any means. For example, an antigen-binding fragment of an antibody may be enzymatically or chemically produced by fragmentation of an intact antibody and/or it may be recombinantly produced from a gene encoding the partial antibody sequence. Alternatively or additionally, antigen-binding fragment of an antibody may be wholly or partially synthetically produced. An antigen-binding fragment of an antibody may optionally comprise a single chain antibody fragment. Alternatively or additionally, an antigen-binding fragment of an antibody may comprise multiple chains that are linked together, for example, by disulfide linkages. An antigen-binding fragment of an antibody may optionally comprise a multi-molecular complex. A functional antibody fragment typically comprises at least about 50 amino acids and more typically comprises at least about 200 amino acids.

Antibody or fragment thereof: As used herein, an "antibody or fragment thereof" refers to an antibody or antibody fragment as defined above.

Humanized antibodies: Humanized antibodies are antibodies from non-human species whose protein sequences have been modified to increase their similarity to antibody variants produced naturally in humans.

IMGT: the international ImMunoGeneTics information system, is an international reference in immunogenetics and immunoinformatics.

Single-chain Fv (scFv): Single-chain Fvs (scFvs) are widely known and used in the art. A single-chain Fv is a fusion protein of the variable regions of the heavy (VH) and light chains (VL) of immunoglobulins, often connected by a short linker peptide (see, e.g., see, e.g., Benny K. C. Lo (ed.), Antibody Engineering—Methods and Protocols, Humana Press 2004, and references cited therein).

FIGURES

FIG. 3 shows TIM1 and CTLD constructs with furin inhibitor payload.

Figure 4:
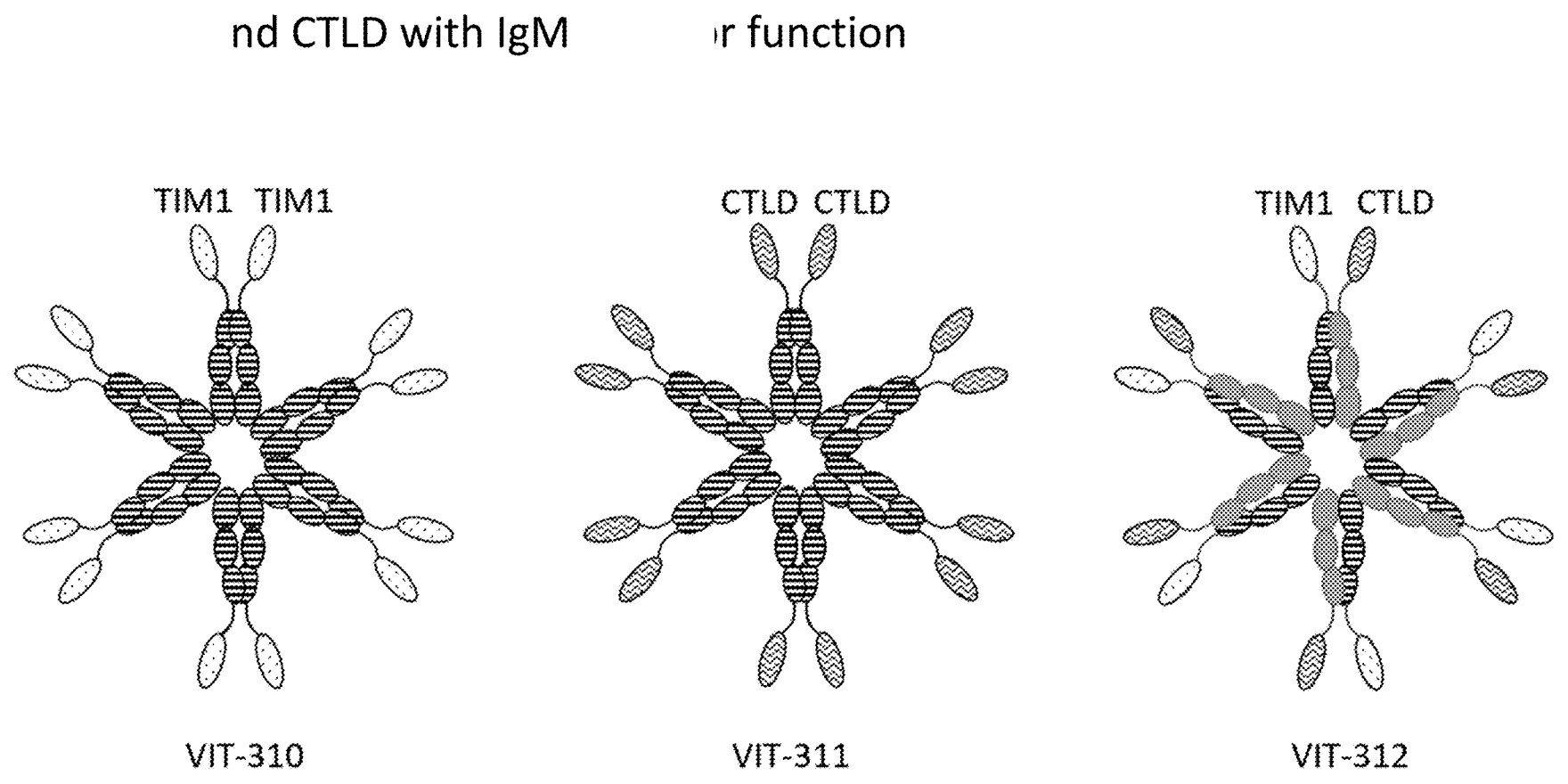

FIG. 4 shows TIM1 and CTLD constructs with IgM effector function.

Figure 1:
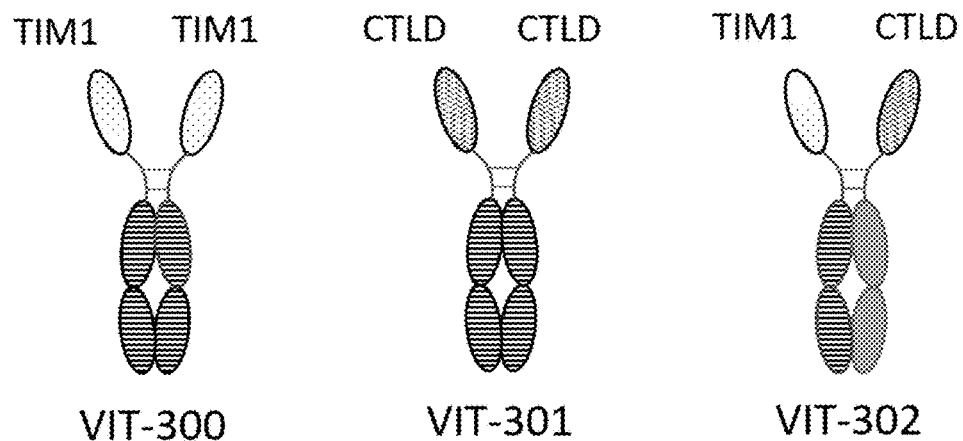
FIG. 1 shows TIM1 and CTLD constructs with enhanced ADCC, ADCP and CDC.

All cited references are incorporated by reference.

The accompanying Figures and Examples are provided to explain rather than limit the present invention. It will be clear to the person skilled in the art that aspects, embodiments, claims and any items of the present invention may be combined.

Unless otherwise mentioned, all percentages are in weight/weight. Unless otherwise mentioned, all measurements are conducted under standard conditions (ambient temperature and pressure). Unless otherwise mentioned, test conditions are according to European Pharmacopoeia 8.0.

EXAMPLES

Example 1: Selection of Recombinant Human TIM1 Fragment

Construct V-TIM1-1 was selected as residues 21-125 of the full length TIM-1 sequence (https://www.uniprot.org/uniprot/Q96D42), and V-TIM1-2 was selected as residues 21-127. V-TIM-2 contains an extra two Pro residues at the C-terminal domain boundary.

TABLE 1

Sequences of Recombinant human TIM1 fragment

| Construct | Sequence | Mw | Predicted pI |
|---|---|---|---|
| V-TIM1-1 | SVKVGGEAGPSVTLPCHYSGAVTSMCWNRGSCSLFTCQNGIV WTNGTHVTYRKDTRYKLLGDLSRRDVSLTIENTAVSDSGVYCC RVEHRGWFNDMKITVSLEIV SEQ. ID No.: 1 | 11.6 KDa | 8.26 |
| V-TIM1-2 | SVKVGGEAGPSVTLPCHYSGAVTSMCWNRGSCSLFTCQNGIV WTNGTHVTYRKDTRYKLLGDLSRRDVSLTIENTAVSDSGVYCC RVEHRGWFNDMKITVSLEIVPP SEQ. ID No.: 2 | 11.8 KDa | 8.26 |

Example 2: Selection of Recombinant Human C-Type Lectin Domain (CTLD) Fragment of DC-SIGN (Cd209)

Construct V-CTLD-1 was selected as residues 250-385 of the full length DC-SIGN sequence (https://www.uniprot.org/uniprot/Q9NNX6), and V-CTLD-2 was selected as residues 254-383. V-CTLD-1 contains 4 internal disulfide bonds, whereas V-CTLD-2 contains 3 internal disulfide bonds.

TABLE 2

Sequences of Recombinant human CTLD fragment of DC-SIGN

| Construct | Sequence | MW | Predicted pI |
|---|---|---|---|
| V-CTLD-1 | ERLCHPCPWEWTFFQGNCYFMSNSQRNWHDSITACKEVGA QLVVIKSAEEQNFLQLQSSRSNRFTWMGLSDLNQEGTWQW VDGSPLLPSFKQYWNRGEPNNVGEEDCAEFSGNGWNDDKC NLAKFWICKKSAASCS SEQ. ID No.: 3 | 15.7 KDa | 5.12 |
| V-CTLD-2 | HPCPWEWTFFQGNCYFMSNSQRNWHDSITACKEVGAQLVV IKSAEEQNFLQLQSSRSNRFTWMGLSDLNQEGTWQWVDGS PLLPSFKQYWNRGEPNNVGEEDCAEFSGNGWNDDKCNLAK FWICKKSAAS SEQ. ID No.: 4 | 15.0 KDa | 5.08 |

Example 3: Design of TIM-1 and CTLD Constructs with IgG3 Effector Functions

Among all human IgG subclasses, IgG3 has the highest effector functions in terms of ADCC, ADCP and CDC (Ref: https://www.frontiersin.org/articles/10.3389/fimmu.2014.00520/full). IgG3 has not typically been used for therapeutics because of the short serum half-life due to proteolytic cleavage of the prolonged hinge region between the CH1 and CH2 domains. To utilize the strong effector functions of the IgG3 subclass, the V-IGG3 construct was designed where the IgG3 hinge (LKTPLGDTTHTPEPKSCDTPPPCPRCPAP) (SEQ ID NO. 6) was replaced with an IgG4 hinge sequence containing an IgG4 hinge S228P mutation to prevent Fab arm exchange (SKYGPPCPPCPAP) (SEQ ID NO. 8) or an IgG1-like hinge (KTGDTTHTCPRCPAP) (SEQ ID NO. 68).

Heterodimeric V-IGG3 constructs were designed based on including K409R (on one half-antibody) and F405L (on second antibody) mutation in the CH3 domains (Reference https://www.nature.com/articles/nprot.2014.169). Each half antibody is first generated as a single homodimer, then mixed together and allowed to recombine as heterodimers under reducing and oxidizing conditions. The resulting sequences are noted as V-IGG3-A and V-IGG3-B and pair together, or V-IGG3-D and V-IGG3-E that pair together. Sequences are found in Table 3, including truncated version that include a (GGGGS)3 linker (SEQ ID NO. 41) to replace the CH1 domains.

TABLE 3

Modified IgG3 domains

| Construct | Sequence | Notes |
|---|---|---|
| WT huIgG3 CH1-CH2-CH3 | ASTKGPSVFPLAPCSRSTSGGTAALGCLVKDYFPEPVTVSW NSGALTSGVHTFPAVLQSSGLYSLSSVVTVPSSSLGTQTYTC NVNHKPSNTKVDKRVE<u>LKTPLGDTTHTPEPKSCDTPPPCPR CPAP</u>ELLGGPSVFLFPPKPKDTLMISRTPEVTCVVVDVSHE DPEVQFKWYVDGVEVHNAKTKPREEQYNSTFRVVSVLTVL HQDWLNGKEYKCKVSNKALPAPIEKTISKTKGQPREPQVY TLPPSREEMTKNQVSLTCLVKGFYPSDIAVEWESSGQPEN NYNTTPPMLDSDGSFFLYSKLTVDKSRWQQGNIFSCSVM HEALHNRFTQKSLSLSPGK SEQ ID No.: 5 | Hinge region underlined as SEQ ID No.: 6 |
| V-IGG3 | ASTKGPSVFPLAPCSRSTSGGTAALGCLVKDYFPEPVTVSW NSGALTSGVHTFPAVLQSSGLYSLSSVVTVPSSSLGTQTYTC NVNHKPSNTKVDKRVE<u>SKYGPPCPPCPAP</u>ELLGGPSVFLFP PKPKDTLMISRTPEVTCVVVDVSHEDPEVQFKWYVDGVEV HNAKTKPREEQYNSTFRVVSVLTVLHQDWLNGKEYKCKVS NKALPAPIEKTISKTKGQPREPQVYTLPPSREEMTKNQVSLT CLVKGFYPSDIAVEWESSGQPENNYNTTPPMLDSDGSFFL YSKLTVDKSRWQQGNIFSCSVMHEALHNRFTQKSLSLSPG K SEQ ID No.: 7 | Hinge region underlined (SEQ ID No.: 8) with IgG4 hinge S228P mutation in bold |
| V-IGG3-Fc | *GGGGSGGGGSGGGGS*<u>KYGPPCPPCPAP</u>ELLGGPSVFLFPP KPKDTLMISRTPEVTCVVVDVSHEDPEVQFKWYVDGVEV HNAKTKPREEQYNSTFRVVSVLTVLHQDWLNGKEYKCKVS NKALPAPIEKTISKTKGQPREPQVYTLPPSREEMTKNQVSLT CLVKGFYPSDIAVEWESSGQPENNYNTTPPMLDSDGSFFL YSKLTVDKSRWQQGNIFSCSVMHEALHNRFTQKSLSLSPG K SEQ ID No.: 9 | Same as above, but with linker and fc only |
| V-IGG3-A | ASTKGPSVFPLAPCSRSTSGGTAALGCLVKDYFPEPVTVSW NSGALTSGVHTFPAVLQSSGLYSLSSVVTVPSSSLGTQTYTC NVNHKPSNTKVDKRVESKYGPPCPPCPAPELLGGPSVFLFP PKPKDTLMISRTPEVTCVVVDVSHEDPEVQFKWYVDGVEV HNAKTKPREEQYNSTFRVVSVLTVLHQDWLNGKEYKCKVS NKALPAPIEKTISKTKGQPREPQVYTLPPSREEMTKNQVSLT CLVKGFYPSDIAVEWESSGQPENNYNTTPPMLDSDGSFFL YSRLTVDKSRWQQGNIFSCSVMHEALHNRFTQKSLSLSPG K SEQ ID No.: 10 | K409R |
| V-IGG3-A-Fc | *GGGGSGGGGSGGGGS*KYGPPCPPCPAPELLGGPSVFLFPP KPKDTLMISRTPEVTCVVVDVSHEDPEVQFKWYVDGVEV HNAKTKPREEQYNSTFRVVSVLTVLHQDWLNGKEYKCKVS NKALPAPIEKTISKTKGQPREPQVYTLPPSREEMTKNQVSLT CLVKGFYPSDIAVEWESSGQPENNYNTTPPMLDSDGSFFL YSRLTVDKSRWQQGNIFSCSVMHEALHNRFTQKSLSLSPG K SEQ ID No.: 11 | Same as above, but with linker and fc only |
| V-IGG3-B | ASTKGPSVFPLAPCSRSTSGGTAALGCLVKDYFPEPVTVSW NSGALTSGVHTFPAVLQSSGLYSLSSVVTVPSSSLGTQTYTC NVNHKPSNTKVDKRVESKYGPPCPPCPAPELLGGPSVFLFP PKPKDTLMISRTPEVTCVVVDVSHEDPEVQFKWYVDGVEV HNAKTKPREEQYNSTFRVVSVLTVLHQDWLNGKEYKCKVS NKALPAPIEKTISKTKGQPREPQVYTLPPSREEMTKNQVSLT CLVKGFYPSDIAVEWESSGQPENNYNTTPPMLDSDGSFLL YSKLTVDKSRWQQGNIFSCSVMHEALHNRFTQKSLSLSPG K SEQ ID No.: 12 | F405L |

TABLE 3-continued

Modified IgG3 domains

| Construct | Sequence | Notes |
|---|---|---|
| V-IGG3-B-Fc | *GGGGSGGGGSGGGGS*KYGPPCPPCPAPELLGGPSVFLFPP KPKDTLMISRTPEVTCVVVDVSHEDPEVQFKWYVDGVEV HNAKTKPREEQYNSTFRVVSVLTVLHQDWLNGKEYKCKVS NKALPAPIEKTISKTKGQPREPQVYTLPPSREEMTKNQVSLT CLVKGFYPSDIAVEWESSGQPENNYNTTPPMLDSDGSFLL YSKLTVDKSRWQQGNIFSCSVMHEALHNRFTQKSLSLSPG K SEQ ID No.: 13 | Same as above, but with linker and fc only |
| V-IGG3-C | ASTKGPSVFPLAPCSRSTSGGTAALGCLVKDYFPEPVTVSW NSGALTSGVHTFPAVLQSSGLYSLSSVVTVPSSSLGTQTYTC NVNHKPSNTKVDKRVEL<u>KTGDTTHTCPRCPAP</u>ELLGGPSV FLFPPKPKDTLMISRTPEVTCVVVDVSHEDPEVQFKWYVD GVEVHNAKTKPREEQYNSTFRVVSVLTVLHQDWLNGKEY KCKVSNKALPAPIEKTISKTKGQPREPQVYTLPPSREEMTKN QVSLTCLVKGFYPSDIAVEWESSGQPENNYNTTPPMLDSD GSFFLYSKLTVDKSRWQQGNIFSCSVMHEALHNRFTQKSL SLSPGK SEQ ID No.: 42 | Utilizes an IgG1-like hinge |
| V-IGG3-C-Fc | *GGGGSGGGGSGGGGS*<u>KTGDTTHTCPRCPAP</u>ELLGGPSVF LFPPKPKDTLMISRTPEVTCVVVDVSHEDPEVQFKWYVDG VEVHNAKTKPREEQYNSTFRVVSVLTVLHQDWLNGKEYKC KVSNKALPAPIEKTISKTKGQPREPQVYTLPPSREEMTKNQ VSLTCLVKGFYPSDIAVEWESSGQPENNYNTTPPMLDSDG SFFLYSKLTVDKSRWQQGNIFSCSVMHEALHNRFTQKSLSL SPGK SEQ ID No.: 43 | Same as above, but with linker and fc only |
| V-IGG3-D | ASTKGPSVFPLAPCSRSTSGGTAALGCLVKDYFPEPVTVSW NSGALTSGVHTFPAVLQSSGLYSLSSVVTVPSSSLGTQTYTC NVNHKPSNTKVDKRVELKTGDTTHTCPRCPAPELLGGPSV FLFPPKPKDTLMISRTPEVTCVVVDVSHEDPEVQFKWYVD GVEVHNAKTKPREEQYNSTFRVVSVLTVLHQDWLNGKEY KCKVSNKALPAPIEKTISKTKGQPREPQVYTLPPSREEMTKN QVSLTCLVKGFYPSDIAVEWESSGQPENNYNTTPPMLDSD GSFFLYSRLTVDKSRWQQGNIFSCSVMHEALHNRFTQKSL SLSPGK SEQ ID No.: 44 | K409R |
| V-IGG3-D-Fc | *GGGGSGGGGSGGGGS*KTGDTTHTCPRCPAPELLGGPSVF LFPPKPKDTLMISRTPEVTCVVVDVSHEDPEVQFKWYVDG VEVHNAKTKPREEQYNSTFRVVSVLTVLHQDWLNGKEYKC KVSNKALPAPIEKTISKTKGQPREPQVYTLPPSREEMTKNQ VSLTCLVKGFYPSDIAVEWESSGQPENNYNTTPPMLDSDG SFFLYSRLTVDKSRWQQGNIFSCSVMHEALHNRFTQKSLSL SPGK SEQ ID No.: 45 | Same as above, but with linker and fc only |
| V-IGG3-E | ASTKGPSVFPLAPCSRSTSGGTAALGCLVKDYFPEPVTVSW NSGALTSGVHTFPAVLQSSGLYSLSSVVTVPSSSLGTQTYTC NVNHKPSNTKVDKRVELKTGDTTHTCPRCPAPELLGGPSV FLFPPKPKDTLMISRTPEVTCVVVDVSHEDPEVQFKWYVD GVEVHNAKTKPREEQYNSTFRVVSVLTVLHQDWLNGKEY KCKVSNKALPAPIEKTISKTKGQPREPQVYTLPPSREEMTKN QVSLTCLVKGFYPSDIAVEWESSGQPENNYNTTPPMLDSD GSFLLYSKLTVDKSRWQQGNIFSCSVMHEALHNRFTQKSL SLSPGK SEQ ID No.: 46 | F405L |
| V-IGG3-E-Fc | *GGGGSGGGGSGGGGS*KTGDTTHTCPRCPAPELLGGPSVF LFPPKPKDTLMISRTPEVTCVVVDVSHEDPEVQFKWYVDG VEVHNAKTKPREEQYNSTFRVVSVLTVLHQDWLNGKEYKC KVSNKALPAPIEKTISKTKGQPREPQVYTLPPSREEMTKNQ VSLTCLVKGFYPSDIAVEWESSGQPENNYNTTPPMLDSDG SFLLYSKLTVDKSRWQQGNIFSCSVMHEALHNRFTQKSLSL SPGK SEQ ID No.: 47 | Same as above, but with linker and fc only |

TIM1 and CTLD fusion proteins were designed with the modified IgG3-Fc domains and are depicted in FIG. 1 and Table 4.

TABLE 4

Sequences of TIM-1 and CTLD constructs with enhanced ADCC, ADCP and CDC

| Construct | Chain 1 | Chain 2 |
|---|---|---|
| VIT-300 | (V-TIM1-1/V-TIM1-2)-V-IGG3-Fc/V-IGG3-C-Fc | Same as Chain 1 |
| VIT-301 | (V-CTLD-1/V-CTLD-2)-V-IGG3-Fc/V-IGG3-C-Fc | Same as Chain 1 |
| VIT-302 | (V-TIM1-1/V-TIM1-2)-V-IGG3-A-Fc/V-IGG3-D-Fc | (V-CTLD-1/V-CTLD-2)-V-IGG3-B-Fc/V-IGG3-E-Fc |

Figure 2:
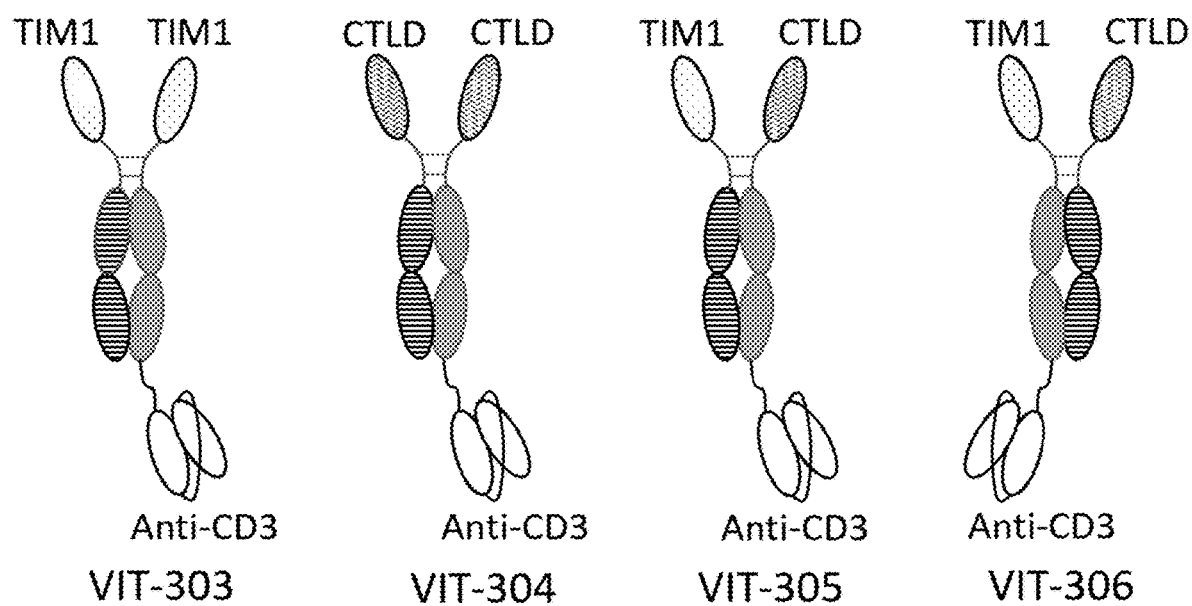
FIG. 2 shows TIM1 and CTLD constructs with T cell engager activity.

Example 4. Design of TIM-1 and CTLD Constructs with T Cell Engaging Activity Additional constructs were designed to engage T cell effector functions by fusing the TIM-1 and CTLD with a single anti-CD3 scFv. The designs are shown in FIG. 2 and Table 5.

Table 5. Sequences of TIM-1 and CTLD Constructs with T Cell Engager Activity

| Construct | Chain 1 | Chain 2 |
|---|---|---|
| VIT-303 | (V-TIM1-1/V-TIM1-2)-(V-IGG4-A-Fc/V-IGG2-A-Fc/V-IGG2-D-Fc) | (V-TIM1-1/V-TIM1-2)-(V-IGG4-B-Fc/V-IGG2-B-Fc/V-IGG2-E-Fc)-GGGGSGGGGSGGGGS (SEQ ID No.: 41)-(anti-CD3 scFv) |
| VIT-304 | (V-CTLD-1/V-CTLD-2)-(V-IGG4-A-Fc/V-IGG2-A-Fc/V-IGG2-D-Fc) | (V-CTLD-1/V-CTLD-2)-(V-IGG4-B-Fc/V-IGG2-B-Fc/V-IGG2-E-Fc)-GGGGSGGGGSGGGGS (SEQ ID No.: 41)-(anti-CD3 scFv) |
| VIT-305 | (V-TIM1-1/V-TIM1-2)-(V-IGG4-A-Fc/V-IGG2-A-Fc/V-IGG2-D-Fc) | (V-CTLD-1/V-CTLD-2)-(V-IGG4-B-Fc/V-IGG2-B-Fc/V-IGG2-E-Fc)-GGGGSGGGGSGGGGS (SEQ ID No.: 41)-(anti-CD3 scFv) |
| VIT-306 | (V-TIM1-1/V-TIM1-2)-(V-IGG4-B-Fc/V-IGG2-B-Fc/V-IGG2-E-Fc)-GGGGSGGGGSGGGGS (SEQ ID No.: 41)-(anti-CD3 scFv) | (V-CTLD-1/V-CTLD-2)-GGGGSGGGGSGGGGS (SEQ ID No.: 41)-(V-IGG4-A-Fc/V-IGG2-A-Fc/V-IGG2-D-Fc) |

Anti-CD3 scFv Sequences are Described Below

| Construct | Sequence |
|---|---|
| VCD3-H1L1 | QVQLVQSGGGVVQPGRSLRLSCAASGYTFTRYTMHWVRQAPGKGLEWVGYINPSRGYTNYNDSV KGRFTISTDKSKNTAYLQMNSLRAEDTAVYYCARYYDDHYSLDYWGQGTTVTVSSGGGGSGGGGS GGGGSGGGGSGGGGSGGGGS DIQMTQSPSSLSASVGDRVTITCQASSSVSYMNWYQQKPGKAPKRWIYDTSKLASGVPSRFSGSGS GTDYTFTISSLQPEDIATYYCQQWSSNPFTFGQGTKLEIK (SEQ ID NO: 18) |
| VCD3-H1L1-DS | QVQLVQSGGGVVQPGRSLRLSCAASGYTFTRYTMHWVRQAPGKCLEWVGYINPSRGYTNYNDSV KGRFTISTDKSKNTAYLQMNSLRAEDTAVYYCARYYDDHYSLDYWGQGTTVTVSSGGGGSGGGGS GGGGSGGGGSGGGGSGGGGS DIQMTQSPSSLSASVGDRVTITCQASSSVSYMNWYQQKPGKAPKRWIYDTSKLASGVPSRFSGSGS GTDYTFTISSLQPEDIATYYCQQWSSNPFTFGCGTKLEIK (SEQ ID NO: 19) |
| VCD3-H1L2 | QVQLVQSGGGVVQPGRSLRLSCAASGYTFTRYTMHWVRQAPGKGLEWVGYINPSRGYTNYNDSV KGRFTISTDKSKNTAYLQMNSLRAEDTAVYYCARYYDDHYSLDYWGQGTTVTVSSGGGGSGGGGS GGGGSGGGGSGGGGSGGGGS EIVLTQSPATLSLSPGERATLSCRASSSVSYMNWYQQKPGQAPRRLIYDTSKRATGIPARFSGSGSGT DYTLTISSLEPEDAAVYYCQQWSSNPFTFGQGTKLEIK (SEQ ID NO: 20) |
| VCD3-H1L2-DS | QVQLVQSGGGVVQPGRSLRLSCAASGYTFTRYTMHWVRQAPGKCLEWVGYINPSRGYTNYNDSV KGRFTISTDKSKNTAYLQMNSLRAEDTAVYYCARYYDDHYSLDYWGQGTTVTVSSGGGGSGGGGS GGGGSGGGGSGGGGSGGGGS EIVLTQSPATLSLSPGERATLSCRASSSVSYMNWYQQKPGQAPRRLIYDTSKRATGIPARFSGSGSGT DYTLTISSLEPEDAAVYYCQQWSSNPFTFGCGTKLEIK (SEQ ID NO: 21) |
| VCD3-H1L3 | QVQLVQSGGGVVQPGRSLRLSCAASGYTFTRYTMHWVRQAPGKGLEWVGYINPSRGYTNYNDSV KGRFTISTDKSKNTAYLQMNSLRAEDTAVYYCARYYDDHYSLDYWGQGTTVTVSSGGGGSGGGGS GGGGSGGGGSGGGGSGGGGS EIQLTQSPATLSLSPGERATLSCRASSSVSYMNWYQQKPGQAPRRWIYDTSKLATGIPARFSGSGSGT DYTLTISSLEPEDAAVYYCQQWSSNPFTFGQGTKLEIK (SEQ ID NO: 22) |
| VCD3-H1L3-DS | QVQLVQSGGGVVQPGRSLRLSCAASGYTFTRYTMHWVRQAPGKCLEWVGYINPSRGYTNYNDSV KGRFTISTDKSKNTAYLQMNSLRAEDTAVYYCARYYDDHYSLDYWGQGTTVTVSSGGGGSGGGGS GGGGSGGGGSGGGGSGGGGS EIQLTQSPATLSLSPGERATLSCRASSSVSYMNWYQQKPGQAPRRWIYDTSKLATGIPARFSGSGSGT DYTLTISSLEPEDAAVYYCQQWSSNPFTFGCGTKLEIK (SEQ ID NO: 23) |
| VCD3-H2L1 | QVQLVQSGAEVKKPGASVKVSCKASGYTFTRYTMHWVRQAPGQGLEWMGYINPSRGYTNYNQKF QGRVTMTTDKSTSTAYMELSSLRSEDTAVYYCARYYDDHYSLDYWGQGTTVTVSSGGGGSGGGGS GGGGSGGGGSGGGGSGGGGS DIQMTQSPSSLSASVGDRVTITCQASSSVSYMNWYQQKPGKAPKRWIYDTSKLASGVPSRFSGSGS GTDYTFTISSLQPEDIATYYCQQWSSNPFTFGQGTKLEIK (SEQ ID NO: 24) |

-continued

| Construct | Sequence |
|---|---|
| VCD3-H2L1-DS | QVQLVQSGAEVKKPGASVKVSCKASGYTFTRYTMHWVRQAPGQCLEWMGYINPSRGYTNYNQKF<br>QGRVTMTTDKSTSTAYMELSSLRSEDTAVYYCARYYDDHYSLDYWGQGTTVTVSS*GGGGSGGGGS*<br>*GGGGSGGGGSGGGGSGGGGS*<br>DIQMTQSPSSLSASVGDRVTITCQASSSVSYMNWYQQKPGKAPKRWIYDTSKLASGVPSRFSGSGS<br>GTDYTFTISSLQPEDIATYYCQQWSSNPFTFGCGTKLEIK(SEQ ID NO: 25) |
| VCD3-H2L2 | QVQLVQSGAEVKKPGASVKVSCKASGYTFTRYTMHWVRQAPGQGLEWMGYINPSRGYTNYNQKF<br>QGRVTMTTDKSTSTAYMELSSLRSEDTAVYYCARYYDDHYSLDYWGQGTTVTVSS*GGGGSGGGGS*<br>*GGGGSGGGGSGGGGSGGGGS*<br>EIVLTQSPATLSLSPGERATLSCRASSSVSYMNWYQQKPGQAPRRLIYDTSKRATGIPARFSGSGSGT<br>DYTLTISSLEPEDAAVYYCQQWSSNPFTFGQGTKLEIK(SEQ ID NO: 26) |
| VCD3-H2L2-DS | QVQLVQSGAEVKKPGASVKVSCKASGYTFTRYTMHWVRQAPGQCLEWMGYINPSRGYTNYNQKF<br>QGRVTMTTDKSTSTAYMELSSLRSEDTAVYYCARYYDDHYSLDYWGQGTTVTVSS*GGGGSGGGGS*<br>*GGGGSGGGGSGGGGSGGGGS*<br>EIVLTQSPATLSLSPGERATLSCRASSSVSYMNWYQQKPGQAPRRLIYDTSKRATGIPARFSGSGSGT<br>DYTLTISSLEPEDAAVYYCQQWSSNPFTFGCGTKLEIK(SEQ ID NO: 27) |
| VCD3-H2L3 | QVQLVQSGAEVKKPGASVKVSCKASGYTFTRYTMHWVRQAPGQGLEWMGYINPSRGYTNYNQKF<br>QGRVTMTTDKSTSTAYMELSSLRSEDTAVYYCARYYDDHYSLDYWGQGTTVTVSS*GGGGSGGGGS*<br>*GGGGSGGGGSGGGGSGGGGS*<br>EIQLTQSPATLSLSPGERATLSCRASSSVSYMNWYQQKPGQAPRRWIYDTSKLATGIPARFSGSGSGT<br>DYTLTISSLEPEDAAVYYCQQWSSNPFTFGQGTKLEIK(SEQ ID NO: 28) |
| VCD3-H2L3-DS | QVQLVQSGAEVKKPGASVKVSCKASGYTFTRYTMHWVRQAPGQCLEWMGYINPSRGYTNYNQKF<br>QGRVTMTTDKSTSTAYMELSSLRSEDTAVYYCARYYDDHYSLDYWGQGTTVTVSS*GGGGSGGGGS*<br>*GGGGSGGGGSGGGGSGGGGS*<br>EIQLTQSPATLSLSPGERATLSCRASSSVSYMNWYQQKPGQAPRRWIYDTSKLATGIPARFSGSGSGT<br>DYTLTISSLEPEDAAVYYCQQWSSNPFTFGCGTKLEIK(SEQ ID NO: 29) |
| VCD3-H3L1 | QVQLVQSGAEVKKPGASVKVSCKASGYTFTRYTMHWVRQSPGQGLEWMGYINPSRGYTNYNQKF<br>QGRVTMTTDKSTSTAYMELSSLRSEDTAVYYCARYYDDHYSLDYWGQGTTVTVSS*GGGGSGGGGS*<br>*GGGGSGGGGSGGGGSGGGGS*<br>DIQMTQSPSSLSASVGDRVTITCQASSSVSYMNWYQQKPGKAPKRWIYDTSKLASGVPSRFSGSGS<br>GTDYTFTISSLQPEDIATYYCQQWSSNPFTFGQGTKLEIK(SEQ ID NO: 30) |
| VCD3-H3L1-DS | QVQLVQSGAEVKKPGASVKVSCKASGYTFTRYTMHWVRQSPGQCLEWMGYINPSRGYTNYNQKF<br>QGRVTMTTDKSTSTAYMELSSLRSEDTAVYYCARYYDDHYSLDYWGQGTTVTVSS*GGGGSGGGGS*<br>*GGGGSGGGGSGGGGSGGGGS*<br>DIQMTQSPSSLSASVGDRVTITCQASSSVSYMNWYQQKPGKAPKRWIYDTSKLASGVPSRFSGSGS<br>GTDYTFTISSLQPEDIATYYCQQWSSNPFTFGCGTKLEIK(SEQ ID NO: 31) |
| VCD3-H3L2 | QVQLVQSGAEVKKPGASVKVSCKASGYTFTRYTMHWVRQSPGQGLEWMGYINPSRGYTNYNQKF<br>QGRVTMTTDKSTSTAYMELSSLRSEDTAVYYCARYYDDHYSLDYWGQGTTVTVSS*GGGGSGGGGS*<br>*GGGGSGGGGSGGGGSGGGGS*<br>EIVLTQSPATLSLSPGERATLSCRASSSVSYMNWYQQKPGQAPRRLIYDTSKRATGIPARFSGSGSGT<br>DYTLTISSLEPEDAAVYYCQQWSSNPFTFGQGTKLEIK(SEQ ID NO: 32) |
| VCD3-H3L2-DS | QVQLVQSGAEVKKPGASVKVSCKASGYTFTRYTMHWVRQSPGQCLEWMGYINPSRGYTNYNQKF<br>QGRVTMTTDKSTSTAYMELSSLRSEDTAVYYCARYYDDHYSLDYWGQGTTVTVSS*GGGGSGGGGS*<br>*GGGGSGGGGSGGGGSGGGGS*<br>EIVLTQSPATLSLSPGERATLSCRASSSVSYMNWYQQKPGQAPRRLIYDTSKRATGIPARFSGSGSGT<br>DYTLTISSLEPEDAAVYYCQQWSSNPFTFGCGTKLEIK(SEQ ID NO: 33) |
| VCD3-H3L3 | QVQLVQSGAEVKKPGASVKVSCKASGYTFTRYTMHWVRQSPGQGLEWMGYINPSRGYTNYNQKF<br>QGRVTMTTDKSTSTAYMELSSLRSEDTAVYYCARYYDDHYSLDYWGQGTTVTVSS*GGGGSGGGGS*<br>*GGGGSGGGGSGGGGSGGGGS*<br>EIQLTQSPATLSLSPGERATLSCRASSSVSYMNWYQQKPGQAPRRWIYDTSKLATGIPARFSGSGSGT<br>DYTLTISSLEPEDAAVYYCQQWSSNPFTFGQGTKLEIK(SEQ ID NO: 34) |
| VCD3-H3L3-DS | QVQLVQSGAEVKKPGASVKVSCKASGYTFTRYTMHWVRQSPGQCLEWMGYINPSRGYTNYNQKF<br>QGRVTMTTDKSTSTAYMELSSLRSEDTAVYYCARYYDDHYSLDYWGQGTTVTVSS*GGGGSGGGGS*<br>*GGGGSGGGGSGGGGSGGGGS*<br>EIQLTQSPATLSLSPGERATLSCRASSSVSYMNWYQQKPGQAPRRWIYDTSKLATGIPARFSGSGSGT<br>DYTLTISSLEPEDAAVYYCQQWSSNPFTFGCGTKLEIK(SEQ ID NO: 35) |

Example 5. Design of TIM-1 and CTLD Constructs with Furin Inhibitor Payload Delivery Site specific addition of drug payloads to the antibody Fc region was devised by analysis of the co-crystal structure of a human IgG1 Fc with the 3-helix bundle of bacterial protein A (PDB structure 5U4Y https://www.rcsb.org/sequence/5U4Y). Computational modelling revealed that A339C would have a stabilizing effect to the structure and S337C or K340C would have a neutral effect to the stability of the Fc domain. A339C was chosen as the site for site specific conjugation.

TABLE 5

IgG4 sequences with engineered free cys for site specific payload conjugation

| Construct | Sequence | Notes |
|---|---|---|
| V-IGG4-ADC-A | ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKYG PPCPPCPAPEAAGGPSVFLPPKPKDTLMISRTP EVTCVVVDVSQEDPEVQFNWYVDGVEVHNAKT KPREEQFNSTYRVVSVLTVLHQDWLNGKEYKCA VSNKGLPSSIEKTISKCKGQPREPQVYTLPPSQEE MTKNQVSLTCLVKGFYPSDIAVEWESNGQPEN NYKTTPPVLDSDGSFFLYSRLTVDKSRWQEGNV FSCSVMHEALHNHYTQKSLSLSLGK SEQ ID No.: 37 | S228P FALA (F234A, L235A) K322A Naturally contains F405 and R409 A339C |
| V-IGG4-ADC-A-Fc | GGGGSGGGGSGGGGSKYGPPCPPCPAPEAAGG PSVFLPPKPKDTLMISRTPEVTCVVVDVSQEDP EVQFNWYVDGVEVHNAKTKPREEQFNSTYRVV SVLTVLHQDWLNGKEYKCAVSNKGLPSSIEKTISK CKGQPREPQVYTLPPSQEEMTKNQVSLTCLVKG FYPSDIAVEWESNGQPENNYKTTPPVLDSDGSFF LYSRLTVDKSRWQEGNVFSCSVMHEALHNHYT QKSLSLSLGK SEQ ID No.: 38 | Same as above, but with linker and fc only |
| V-IGG4-ADC-B | ASTKGPSVFPLAPCSRSTSESTAALGCLVKDYFPE PVTVSWNSGALTSGVHTFPAVLQSSGLYSLSSVV TVPSSSLGTKTYTCNVDHKPSNTKVDKRVESKYG PPCPPCPAPEAAGGPSVFLPPKPKDTLMISRTP EVTCVVVDVSQEDPEVQFNWYVDGVEVHNAKT KPREEQFNSTYRVVSVLTVLHQDWLNGKEYKCA VSNKGLPSSIEKTISKCKGQPREPQVYTLPPSQEE MTKNQVSLTCLVKGFYPSDIAVEWESNGQPEN NYKTTPPVLDSDGSFLLYSKLTVDKSRWQEGNVF SCSVMHEALHNHYTQKSLSLSLGK SEQ ID No.: 39 | S228P FALA (F234A, L235A) K322A F405L, R409K A339C |
| V-IGG4-ADC-B-Fc | GGGGSGGGGSGGGGSKYGPPCPPCPAPEAAGG PSVFLPPKPKDTLMISRTPEVTCVVVDVSQEDP EVQFNWYVDGVEVHNAKTKPREEQFNSTYRVV SVLTVLHQDWLNGKEYKCAVSNKGLPSSIEKTISK CKGQPREPQVYTLPPSQEEMTKNQVSLTCLVKG FYPSDIAVEWESNGQPENNYKTTPPVLDSDGSFL LYSKLTVDKSRWQEGNVFSCSVMHEALHNHYT QKSLSLSLGK SEQ ID No.: 40 | Same as above, but with linker and fc only |

TIM1 and CTLD fusion proteins with Fc domain with payload conjugation sites were designed and are shown in FIG. 3 and Table 6.

TABLE 6

Sequences of TIM1 and CTLD therapeutic proteins with free cys for payload conjugation

| Construct | Chain 1 | Chain 2 |
|---|---|---|
| VIT-307 | (V-TIM1-1/V-TIM1-2)- V-IGG4-ADC-A-Fc | Same as Chain 1 |
| VIT-308 | (V-CTLD-1/V-CTLD-2)- V-IGG4-ADC-A-Fc | Same as Chain 1 |
| VIT-309 | (V-TIM1-1/V-TIM1-2)- V-IGG4-ADC-A-Fc | (V-CTLD-1/V-CTLD-2)- V-IGG4-ADC-B-Fc |

Example 6. Furin Linkers

Decanoyl-Arg-Val-Lys-Arg-chloromethylketone (dec-RVKR-cmk) (SEQ ID NO. 81) or hexa-D-arginine (D6R) were linked to TIM-1 and CTLD constructs using cleavable linkers such as acid sensitive N-acyl-hydrazone or enzyme sensitive malemeide-conjugated dipeptides, valine-alanine, valine-citrulline, or phenylalanine-Lysine.

Acid sensitive linkers are cleaved in the lysosome acidic environment after internalization of the construct. This strategy has been used in two approved ADCs, Gemtuzumab ozogamicin and Inotuzumab ozogamicin. Lysosomal protease sensitive dipeptides release the drug after cleavage by proteases such as cathepsin B-lysosomal protease. This type of linker chemistry has been used for FDA approved Brentuximab vedotin.

Linkage to the polypeptide of antibodies is done through the nucleophilic groups of lysine or cysteine by random conjugation, generating a heterogeneous mixture of conjugates, or by site-directed conjugation to engineered cysteines, reducing the heterogeneity of the product to an antibody-drug ratio (ADR) of 1 or 2.

The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in maleimide reagents may react with amine groups, but higher pH (>9.0) and longer reaction times are required (Garman, 1997, Non-Radioactive Labelling: A Practical Approach, Academic Press, London).

The first FDA approved site-directed ADC through engineered cysteines was vadastuximab talirine (Seattle Genetics).

Sequence of human IgM constant region, numbered residues 1-453 by uniprot (www_uniprot.org/uniprot/P01871):

SEQ ID No.: 64
GSASAPTLFPLVSCENSPSDTSSVAVGCLAQDFLPDSITFSWKYKNNSD

ISSTRGFPSVLRGGKYAATSQVLLPSKDVMQGTDEHVVCKVQHPNGNKE

KNVPLPVIAELPPKVSVFVPPRDGFFGNPRKSKLICQATGFSPRQIQVS

WLREGKQVGSGVTTDQVQAEAKESGPTTYKVTSTLTIKESDWLGQSMFT

CRVDHRGLTFQQNASSMCVPDQDTAIRVFAIPPSFASIFLTKSTKLTCL

VTDLTTYDSVTISWTRQNGEAVKTHTNISESHPNATFSAVGEASICEDD

WNSGERFTCTVTHTDLPSPLKQTISRPKGVALHRPDVYLLPPAREQLNL

RESATITCLVTGFSPADVFVQWMQRGQPLSPEKYVTSAPMPEPQAPGRY

FAHSILTVSEEEWNTGETYTCVVAHEALPNRVTERTVDKSTGKPTLYNV

SLVMSDTAGTCY

TABLE 7

Linker Chemistry

| Residue | Spacer 1 | Linker | Spacer 2 | Drug |
| --- | --- | --- | --- | --- |
| Cysteine, engineered Cysteine | Maleimidocaproyl (mc), maleimidomethyl cyclohexane-1-carboxylate | VC, VA, PL | para-amino benzyloxycarbonyl (PABC) | hexa-D-arginine, dec-RVKR-cmk (comprising SEQ. ID NO. 81) |
| Lysine | NA | N-acyl-hydrozone, N-succinimidyl-4-(2-pyridyldithio)Butanoate-disulfide (SPDB-disulfide), maleimidomethyl cyclohexane-1-carboxylate, sulfo-SPDB | NA | hexa-D-arginine, dec-RVKR-cmk (comprising SEQ. ID NO. 81) |

Spacer 1: The purpose of the mc spacer is to provide enough room so that the vc group can be recognized by cathepsin B, which cleaves the citrulline-PABC amide bond.

Spacer 2: Self-immolative spacer

Example 7. Fusion Proteins with IgM Constant Regions

IgM molecules have robust Fc effector functions, particularly with CDC. IgM molecules naturally homodimerize and then covalently associate into pentamers or hexamers. IgM do not contain hinge regions like IgG molecules and instead contain an extra CH domain (CH1-CH2-CH3-CH4). The homodimeric heavy chains come together at the CH2 and CH4 domains. Based on visual analyses of the crystal structure of the murine IgM CH2 domain (pdb 4JVU), the crystal structure of the murine IgM CH4 domain (pdb 4JVW), and a sequence alignment of the human IgM CH2 and CH4 sequences with the homologous mouse sequences, mutations were designed to induce IgM heavy chain heterodimerization by inducing charge differences at the homodimerization interfaces.

Sequence of IgM CH2-CH3-CH4 which can used for fusing to antibody fragments (Fab, scFv, VHH, etc) or targeting proteins (TIM-1, CTLD/DC-SIGN) for adding IgM effector functions (residues 105-453):

V-IGM

SEQ. ID No.: 65
VIAELPPKVSVFVPPRDGFFGNPRKSKLICQATGFSPRQIQVSWLREGK

QVGSGVTTDQVQAEAKESGPTTYKVTSTLTIKESDWLGQSMFTCRVDHR

GLTFQQNASSMCVPDQDTAIRVFAIPPSFASIFLTKSTKLTCLVTDLTT

YDSVTISWTRQNGEAVKTHTNISESHPNATFSAVGEASICEDDWNSGER

FTCTVTHTDLPSPLKQTISRPKGVALHRPDVYLLPPAREQLNLRESATI

TCLVTGFSPADVFVQWMQRGQPLSPEKYVTSAPMPEPQAPGRYFAHSIL

TVSEEEWNTGETYTCVVAHEALPNRVTERTVDKSTGKPTLYNVSLVMSD

TAGTCY

Based on the structural analysis, the underlined residues K131 and Q135 were found to be in close proximity in the CH2:CH2 interface, and residues T354 and E385 were found to be in close proximity in the CH4:CH4 interface. The following mutations were made to alter the charge pattern in V-IGM-A and V-IGM-B to induce heterodimer formation of A:B and repel the formations of A:A or B:B.

TABLE 8

IgM constant region mutations to induce heavy chain heterodimer formation

| Position | Wildtype residue in V-IGM | V-IGM-A | V-IGM-B |
|---|---|---|---|
| 131 | K | K/R/H | D/E |
| 135 | Q | K/R/H | D/E |
| 354 | T | D/E | K/R/H |
| 385 | E | D/E | K/R/H |

TIM1 and CTLD fusion proteins with IgM effector functions were designed and shown in Table 9.

TABLE 9

Sequences of TIM1 and CTLD therapeutic proteins with IgM effector functions

| Construct | Chain 1 | Chain 2 |
|---|---|---|
| VIT-310 | (V-TIM1-1/V-TIM1-2)-GGGGSGGGGSGGGGS (SEQ ID No.: 41)- V-IGM | Same as Chain 1 |
| VIT-311 | (V-CTLD-1/V-CTLD-2)-GGGGSGGGGSGGGGS (SEQ ID No.: 41)- V-IGM | Same as Chain 1 |
| VIT-312 | (V-TIM1-1/V-TIM1-2)-GGGGSGGGGSGGGGS (SEQ ID No.: 41)- V-IGM-A | (V-CTLD-1/V-CTLD-2)-GGGGSGGGGSGGGGS (SEQ ID No.: 41)- V-IGM-B |

The invention is further described by the following items:
1. A fusion construct comprising an Ig-Fc domain or other protein scaffold, such as albumin or an antibody fragment binding to albumin, and
   a. a peptide, protein or antibody fragment binding to phosphatidylserine and/or
   b. a peptide or protein binding to and/or recognizing a PAMP expressed by a microbe.
2. A fusion construct, preferably according to any of the preceding items comprising an IgG-Fc domain or other protein scaffold and
   a. a recombinant human TIM1 fragment and/or
   b. a recombinant human CD209 fragment.
3. A fusion construct, preferably according to any of the preceding items comprising an IgG-Fc domain or other protein scaffold and
   a. a recombinant human TIM1 fragment and/or
   b. a recombinant human CD209 fragment
   and wherein said fusion construct provides enhanced ADCC, ADCP and/or CDC.
4. A fusion construct, preferably according to any of the preceding items comprising an IgG-Fc domain or other protein scaffold and
   a. a recombinant human TIM1 fragment and/or
   b. a recombinant human CD209 fragment
   and wherein said fusion construct additionally comprises the CDR regions according to SEQ ID No.: 54-59.
5. A fusion construct, preferably according to any of the preceding items comprising an IgG-Fc domain or other protein scaffold and
   a. a recombinant human TIM1 fragment and/or
   b. a recombinant human CD209 fragment
   and wherein said fusion construct further comprises a Furin inhibitor.
6. The fusion construct according to any of the preceding items, wherein said peptide, protein or antibody fragment is capable of binding to and/or stimulating an immune cell.
7. The fusion construct according to any of the preceding items, wherein said TIM1 fragment has a sequence length selected from the group consisting of 40-200 amino acid residues, 50-180 amino acid residues, 60-160 amino acid residues, 70-140 amino acid residues, 80-130 amino acid residues, 90-120 amino acid residues, 100-120 amino acid residues and 100-110 amino acid residues.
8. The fusion construct according to any of the preceding items, wherein said CD209 fragment has a sequence length selected from the group consisting of 40-200 amino acid residues, 40-190 amino acid residues, 50-180 amino acid residues, 60-170 amino acid residues, 70-160 amino acid residues, 80-150 amino acid residues, 90-150 amino acid residues, 100-150 amino acid residues, 110-150 amino acid residues, 120-150 amino acid residues and 130-140 amino acid residues.
9. The fusion construct according to any of the preceding items, wherein said TIM1 and/or CD209 fragment has a sequence homology of at least 70%, alternatively 75%, alternatively 80%, alternatively 85%, alternatively 90%, alternatively 95% to wildtype TIM1 or CD209.
10. The fusion construct according to any of the preceding items, wherein said TIM1 and/or CD209 fragment has intact TIM1 and/or CD209 function.
11. The fusion construct according to any of the preceding items, wherein said IgG-Fc domain is an IgG3-Fc domain.
12. The fusion construct according to any of the preceding items, comprising additionally at least one of the following:
    a) An IgG3, wherein the hinge sequence has been replaced, preferably with an IgG4 or IgG1 hinge sequence;
    b) CDR regions according to SEQ ID No.: 54-59; and/or
    c) A furin inhibitor.
13. The fusion construct according to any of the preceding items, wherein said fusion construct comprises a sequence according to SEQ ID No.: 1 and/or SEQ ID No.: 2.
14. The fusion construct according to any of the preceding items, wherein said fusion construct comprises a sequence according to SEQ ID No.: 3 and/or SEQ ID No.: 4.
15. The fusion construct according to any of the preceding items, wherein said fusion construct comprises at least 1, at least 2, at least 3, at least 4, at least 5, at least 6, at least 7 or preferably at least 8 disulfide bonds.
16. The fusion construct according to any of the preceding items, wherein said fusion construct is capable of binding to a target, and wherein said target is a mannan, a high-mannose containing structure, a fucan, a phospholipid phosphatidylserine and/or CD3.

17. The fusion construct according to any of the preceding items, wherein said fusion construct comprises:
    a. A first chain comprising
        i. a sequence according to SEQ ID No.: 1 or SEQ ID No.: 2 and
        ii. a sequence according to SEQ ID No.: 9 or a sequence according to SEQ ID No.: 43, and
    b. A second chain comprising
        iii. a sequence according to SEQ ID No.: 1 or SEQ ID No.: 2, and
        iv. a sequence according to SEQ ID No.: 9 or a sequence according to SEQ ID No.: 43.
18. The fusion construct according to any of the preceding items, wherein said fusion construct comprises:
    a. A first chain comprising
        i. a sequence according to SEQ ID No.: 3 or SEQ ID No.: 4, and
        ii. a sequence according to SEQ ID No.: 9 or a sequence according to SEQ ID No.: 43, and
    b. A second chain comprising
        iii. a sequence according to SEQ ID SEQ ID No.: 3 or SEQ ID No.: 4, and
        iv. a sequence according to SEQ ID No.: 9 or a sequence according to SEQ ID No.: 43.
19. The fusion construct according to any of the preceding items, wherein said fusion construct comprises:
    a. A first chain comprising
        i. a sequence according to SEQ ID No.: 1 or SEQ ID No.: 2, and
        ii. a sequence according to SEQ ID No.: 11 or a sequence according to SEQ ID No.: 45, and
    b. A second chain comprising
        iii. a sequence according to SEQ ID No.: 3 or SEQ ID No.: 4, and
        iv. a sequence according to SEQ ID No.: 13 or a sequence according to SEQ ID No.: 47.
20. The fusion construct according to any of the preceding items, wherein said fusion construct comprises:
    a. A first chain comprising
        i. a sequence according to SEQ ID No.: 1 or SEQ ID No.: 2, and
        ii. a sequence according to SEQ ID No.: 14 or 15, or SEQ ID No.: 66, and
    b. A second chain comprising
        iii. a sequence according to SEQ ID No.: 1 or SEQ ID No.: 2, and
        iv. a sequence according to SEQ ID No.: 16 or 17, or SEQ ID No.: 67 and
        v. a linker sequence, preferably according to SEQ ID No.: 41, and
        vi. a sequence according to any of the sequences selected among SEQ ID No.: 18-35.
21. The fusion construct according to any of the preceding items, wherein said fusion construct comprises:
    a. A first chain comprising
        i. a sequence according to SEQ ID No.: 3 or SEQ ID No.: 4, and
        ii. a sequence according to SEQ ID No.: 14 or 15, or SEQ ID No.: 66, and
    b. A second chain comprising
        iii. a sequence according to SEQ ID No.: 3 and/or SEQ ID No.: 4, and
        iv. a sequence according to SEQ ID No.: 16 or 17, or SEQ ID No.: 67 and
        v. a linker sequence preferably according to SEQ ID No.: 41, and
        vi. a sequence according to any of the sequences selected among SEQ ID No.: 18-35.
22. The fusion construct according to any of the preceding items, wherein said fusion construct comprises:
    a. A first chain comprising
        i. a sequence according to SEQ ID No.: 1 or SEQ ID No.: 2, and
        ii. a sequence according to SEQ ID No.: 14 or 15, or SEQ ID No.: 66, and
    b. A second chain comprising
        iii. a sequence according to SEQ ID No.: 3 or SEQ ID No.: 4, and
        iv. a sequence according to SEQ ID No.: 16 or 17, or SEQ ID No.: 67, and
        v. a linker sequence preferably according to SEQ ID No.: 41, and
        vi. a sequence according to any of the sequences selected among SEQ ID No.: 18-35.
23. The fusion construct according to any of the preceding items, wherein said fusion construct comprises
    a. A first chain comprising
        i. a sequence according to SEQ ID No.: 1 or SEQ ID No.: 2, and
        ii. a sequence according to SEQ ID No.: 16 or 17, or SEQ ID No.: 67, and
        iii. a linker sequence preferably according to SEQ ID No.: 41, and
        iv. a sequence according to any of the sequences selected among SEQ ID No.: 18-35, and
    b. A second chain comprising
        v. a sequence according to SEQ ID No.: 3 or SEQ ID No.: 4,
        vi. a linker sequence preferably according to SEQ ID No.: 41, and
        vii. a sequence according SEQ ID No.: 14 or 15, or SEQ ID No.: 66.
24. The fusion construct according to any of the preceding items, wherein said fusion construct comprises a linker.
25. The fusion construct according to any of the preceding items, wherein said linker is selected among a (GGGGS)3 linker (SEQ ID NO. 41), a (GGGGS)4 linker (SEQ ID NO. 70), a (GGGGS)5 linker (SEQ ID NO. 71) and a (GGGGS)6 linker (SEQ ID NO. 72).
26. The fusion construct according to any of the preceding items, wherein said fusion construct comprises at least one free cysteine residue, at least two free cysteine residues, at least three free cysteine residues, at least four free cysteine residues, at least five free cysteine residues or preferably at least six free cysteine residues.
27. The fusion construct according to any of the preceding items, wherein said free cysteine allows interaction with a drug and/or a payload.
28. The fusion construct according to any of the preceding items, wherein said payload is a furin inhibitor.
29. The fusion construct according to any of the preceding items, wherein said fusion construct comprises a A339C mutation, a S337C mutation and/or a K340C mutation.
30. The fusion construct according to any of the preceding items, wherein said fusion construct comprises a sequence selected among any of the sequences SEQ ID No.: 36, 37, SEQ ID No.: 38, 39, 40, 42, 44 or 46.
31. The fusion construct according to any of the preceding items, wherein said fusion construct is an IgG1, IgG2, IgG3 or an IgG4.

32. The fusion construct according to any of the preceding items, wherein said fusion construct is an IgG, IgM, IgA, IgD or an IgE.
33. The fusion construct according to any of the preceding items, wherein said fusion construct comprises a null fc.
34. The fusion construct according to any of the preceding items, wherein said null fc comprises an Ala substitution at position 234 and/or Ala substitution at 235, and/or N297A, and/or a K322A mutation.
35. The fusion construct according to any of the preceding items, wherein said fusion construct comprises a heterodimerization domain.
36. The fusion construct according to any of the preceding items, wherein said heterodimerization domain comprises a sequence according to SEQ ID No.: 48, 49 or 50.
37. The fusion construct according to any of the preceding items, wherein said fusion construct comprises a heterodimerization mutation.
38. The fusion construct according to any of the preceding items, wherein said heterodimerization mutation is an F405L, R409K and/or K409R mutation.
39. The fusion construct according to any of the preceding items, wherein said fusion construct comprises:
    a. A first chain comprising
        i. a sequence according to SEQ ID No.: 1 or SEQ ID No.: 2, and
        ii. a sequence according to SEQ ID No.: 38, and
    b. A second chain comprising
        iii. a sequence according to SEQ ID No.: 1 or SEQ ID No.: 2, and
        iv. a sequence according to SEQ ID No.: 38.
40. The fusion construct according to any of the preceding items, wherein said fusion construct comprises:
    a. A first chain comprising
        i. a sequence according to SEQ ID No.: 3 or SEQ ID No.: 4, and
        ii. a sequence according to SEQ ID No.: 38, and
    b. A second chain comprising
        iii. a sequence according to SEQ ID No.: 3 or SEQ ID No.: 4, and
        iv. a sequence according to SEQ ID No.: 38.
41. The fusion construct according to any of the preceding items, wherein said fusion construct comprises:
    a. A first chain comprising
        i. a sequence according to SEQ ID No.: 1 or SEQ ID No.: 2, and
        ii. a sequence according to SEQ ID No.: 38, and
    b. A second chain comprising
        iii. a sequence according to SEQ ID No.: 3 or SEQ ID No.: 4, and
        iv. a sequence according to SEQ ID No.: 40.
42. The fusion construct according to any of the preceding items, wherein said fusion construct comprises:
    c. A first chain comprising
        i. a sequence according to SEQ ID No.: 1 or SEQ ID No.: 2, and
        ii. a linker sequence according to SEQ ID No.: 41, and
        iii. a sequence according to SEQ ID No.: 65
    d. A second chain comprising
        iv. a sequence according to SEQ ID No.: 1 or SEQ ID No.: 2, and
        v. a linker sequence according to SEQ ID No.: 41, and
        vi. a sequence according to SEQ ID No.: 65
43. The fusion construct according to any of the preceding items, wherein said fusion construct comprises:
    a. A first chain comprising
        i. a sequence according to SEQ ID No.: 3 or SEQ ID No.:, and
        ii. a linker sequence according to SEQ ID No.: 41, and
        iii. a sequence according to SEQ ID No.: 65
    b. A second chain comprising
        iv. a sequence according to SEQ ID No.: 3 or SEQ ID No.: 4, and
        v. a linker sequence according to SEQ ID No.: 41, and
        vi. a sequence according to SEQ ID No.: 65
44. The fusion construct according to any of the preceding items, wherein said fusion construct comprises:
    a. A first chain comprising
        i. a sequence according to SEQ ID No.: 1 or SEQ ID No.: 2, and
        ii. a linker sequence according to SEQ ID No.: 41, and
        iii. a sequence according to SEQ ID No.: 65, wherein said sequence ID No.: 65 comprises one or more of the mutations of table 8
    b. A second chain comprising
        iv. a sequence according to SEQ ID No.: 3 or SEQ ID No.: 4 and
        v. a linker sequence according to SEQ ID No.: 41, and
        vi. a sequence according to SEQ ID No.: 65, wherein said sequence ID No.: 65 comprises one or more of the mutations of table 8.
45. The fusion construct according to any of the preceding items, wherein the ratio of fusion construct to said drug and/or payload is selected among 1, 2, 3, 4, 5, 6, 7, 8, 9 or 10.
46. The fusion construct according to any of the preceding items, wherein said fusion construct comprises a kappa light chain according to SEQ ID No.: 51 or a lambda light chain according to SEQ ID No.: 52 or 53.
47. A fusion construct, preferably according to any of the preceding items, wherein said fusion construct is an IgG3 construct, and wherein said IgG3 construct comprises a hinge region, wherein said hinge region has been modified.
48. The fusion construct according to any of the preceding items, wherein said hinge region comprises a sequence having a total of at least 10% identity, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identity to the sequence according to SEQ ID No.: 6 or SEQ ID No.: 8.
49. The fusion construct according to any of the preceding items, wherein said fusion construct comprises the sequence according to SEQ ID No.: 5, 7, 9, 10, 11, 12 and/or 13.
50. The fusion construct according to any of the preceding items, wherein said hinge region comprises at least one free cysteine residue, at least two free cysteine residues or preferably at least three free cysteine residues.
51. The fusion construct according to any of the preceding items, wherein said hinge region comprises a S228P mutation.

52. The fusion construct according to any of the preceding items, wherein said hinge region comprises a sequence according to SEQ ID No.: 6 and/or SEQ ID No.: 8 and/or SEQ ID No.: 68
53. The fusion construct according to any of the preceding items, wherein said fusion construct is used to detect phosphatidylserine.
54. The fusion construct according to any of the preceding items, wherein said fusion construct is used to detect phosphatidylserine in the blood of a subject.
55. The fusion construct according to item 53, wherein said fusion construct comprises a sequence according to SEQ ID No.: 1, and/or a sequence according to SEQ ID No.: 2.
56. The fusion construct according to any of the preceding items, wherein said fusion construct is used to detect C-type lectin binding mannan or fucan moieties.
57. The fusion construct according to any of the preceding items, wherein said fusion construct is used to detect C-type lectin binding mannan or fucan moieties in the blood of a subject.
58. The fusion construct according to item 56, wherein said fusion construct comprises a sequence according to SEQ ID No.: 3 and/or a sequence according to SEQ ID No.: 4.
59. A fusion construct, a fusion protein or an antibody comprising the constant region(s) of IgG3 and a hinge, wherein said hinge preferably is selected among an IgG1 or IgG4 hinge.
60. The fusion construct, fusion protein or antibody according to any of the preceding items, comprising one or more heterodimerization mutations.
61. The fusion construct, fusion protein or antibody according to any of the preceding items, comprising heterodimerization mutations involve positions 405 and/or 409 (EU numbering).
62. IgG3 homodimer comprising a hinge region, wherein said hinge region comprises a sequence selected among SEQ ID No.: 6, 8 and 68.
63. IgG3 heterodimer comprising a hinge region, wherein said hinge region comprises a sequence selected among SEQ ID No.: 6, 8 and 68.
64. IgG3 according to any of the preceding items, wherein said IgG3 comprises a mutation at position 405 and/or position 409.
65. IgM heterodimers obtainable by changing the charge pairs of the CH2 and/or CH4 domains.
66. IgM heterodimers according to any of the preceding items, comprising one or more of the mutations of Table 8.
67. The IgM according to any of the preceding items, wherein said IgM comprises a sequence according to SEQ ID No.: 64 and/or 65.
68. A fusion construct, preferably according to any of the preceding items, wherein said fusion construct comprises an IgG3 homodimer, an IgG3 heterodimer and/or an IgM heterodimer according to any of the preceding items.
69. The fusion construct according to any of the preceding items, wherein said fusion construct is for use in the treatment of an infection.
70. The fusion construct according to any of the preceding items, wherein said infection is an infection caused by a virus, a parasite, a bacteria, a fungi or a protozoon.
71. The fusion construct according to any of the preceding items, wherein said virus is selected among an arbovirus, Zika virus, Dengue virus, West Nile virus, Ebola virus, influenza virus, influenza virus H1N1, Chikungunya virus, enterovirus and Coronaviruses SARS-COV.
72. The fusion construct according to any of the preceding items, wherein said bacteria is selected among *Mycobacterium tuberculosis* and *Mycobacterium leprae*.
73. The fusion construct according to any of the preceding items, wherein said parasite is selected among Leishmaniasis and Malaria.
74. Use of a fusion construct according to any of the preceding items for the treatment of an infection.
75. Use according to any of the preceding items, wherein said infections are selected among viral, bacterial and protozoan infections.
76. Use according to any of the preceding items, wherein the treatment comprising administration of the fusion construct with an administration form selected among subcutaneous, intradermal, intramuscular, oral and nasal.
77. Use of IgG4 or a part of IgG4 for payload delivery, wherein said IgG4 has been modified to comprise no Fc or wherein the activity of the Fc of said IgG4 has been nullified or diminished by one or more mutations.
78. The use according to any of the preceding items, wherein said IgG4 comprises one or more heterodimerization mutations.
79. The use according to any of the preceding items, wherein said IgG4 comprises one or more Cys mutations, preferably thereby allowing site specific conjugation.
80. The use according to any of the preceding items, wherein said IgG4 comprises a Cys at position 339 (EU numbering).
81. A vaccine comprising a fusion construct according to any of the preceding items.
82. A vaccine comprising a mannan, a high-mannose containing structure, a fucan and/or a phospholipid phosphatidylserine (PS).
83. The vaccine according to any of the preceding items further comprising β-glucan.
84. The vaccine according to any of the preceding items, for the prevention and/or treatment of an infection.
85. The vaccine according to any of the preceding items, wherein said infection is coursed by a virus, preferably according to item 71, a parasite, preferably according to item 73, a bacteria, preferably according to item 72, a fungi or a protozoan.
86. The fusion construct and/or vaccine according to any of the preceding items, wherein said fusion construct and/or vaccine allows administration through a route selected among subcutaneous administration, intradermal administration, intramuscular administration, oral administration and/or nasal administration.
87. A composition comprising a fusion construct according to any of the preceding items, optionally comprising one or more excipients such as diluents, binders or carriers.
88. A method of treating and/or preventing an infection in a subject, comprising a step of administration of a fusion construct and/or a vaccine and/or a composition according to any of the preceding item.
89. A method of screening and/or monitoring progression of a disease in a subject, wherein said method comprises the following steps:
   i. Providing a blood sample from said subject.
   ii. Contacting said blood sample with a fusion construct according to any of the preceding items.

90. An isolated nucleic acid molecule encoding a fusion construct according to any of the precedent items.
91. A recombinant vector comprising the nucleic acid molecule of item 90.
92. A host cell comprising the recombinant vector of item 91.
93. A method for the production of a fusion construct according to any of the precedent items comprising a step of culturing the host cell according to item 92 in a culture medium under conditions allowing the expression of the fusion construct and separating the fusion construct from the culture medium.

The invention claimed is:

1. A fusion construct comprising
   an Ig-Fc domain,
   a peptide, protein or antibody fragment binding to phosphatidylserine, wherein the peptide, protein or antibody fragment binding to phosphatidylserine is selected from TIM-1 and fragments thereof,
   a peptide or protein binding to and/or recognizing a PAMP expressed by a microbe, wherein the peptide or protein binding to and/or recognizing a PAMP expressed by a microbe is selected from DC-SIGN and fragments thereof,
   a first chain comprising a sequence according to SEQ ID No.: 1 or SEQ ID No.: 2, and a sequence according to SEQ ID No.: 38, and
   a second chain comprising a sequence according to SEQ ID No.: 3 or SEQ ID No.: 4, and a sequence according to SEQ ID No.: 40.

2. The fusion construct according to claim 1, wherein the Ig-Fc domain is dimeric and comprises heterodimerization mutations involving positions 405 and/or 409 (EU numbering).

3. The fusion construct according to claim 1, wherein said fusion construct is for use in the treatment of an infection.

4. The fusion construct according to claim 3, wherein said infection is an infection caused by a virus, a parasite, a bacteria, a fungi or a protozoan.

5. The fusion construct according to claim 4, wherein said virus is selected among an arborvirus, Zika virus, Dengue virus, West Nile virus, Ebola virus, influenza virus, influenza virus H1N1, Chikungunya virus, enterovirus, Coronavirus SARS-COV-2 and Coronaviruses SARS-COV.

6. The fusion construct according to claim 4, wherein said bacteria is selected among *Mycobacterium tuberculosis* and *Mycobacterium leprae*.

7. The fusion construct according to claim 4, wherein said parasite is selected among Leishmaniasis and Malaria.

8. The fusion construct according to claim 1, wherein said fusion construct allows administration through a route selected among subcutaneous administration, intradermal administration, intramuscular administration, oral administration and/or nasal administration.

* * * * *

SEQUENCE LISTING

```
<160> NUMBER OF SEQ ID NOS: 81

<210> SEQ ID NO 1
<211> LENGTH: 105
<212> TYPE: PRT
<213> ORGANISM: Artificial Sequence
<220> FEATURE:
<223> OTHER INFORMATION: V-TIM1-1

<400> SEQUENCE: 1

Ser Val Lys Val Gly Gly Glu Ala Gly Pro Ser Val Thr Leu Pro Cys
1               5                   10                  15

His Tyr Ser Gly Ala Val Thr Ser Met Cys Trp Asn Arg Gly Ser Cys
            20                  25                  30

Ser Leu Phe Thr Cys Gln Asn Gly Ile Val Trp Thr Asn Gly Thr His
        35                  40                  45

Val Thr Tyr Arg Lys Asp Thr Arg Tyr Lys Leu Leu Gly Asp Leu Ser
    50                  55                  60

Arg Arg Asp Val Ser Leu Thr Ile Glu Asn Thr Ala Val Ser Asp Ser
65                  70                  75                  80

Gly Val Tyr Cys Cys Arg Val Glu His Arg Gly Trp Phe Asn Asp Met
                85                  90                  95

Lys Ile Thr Val Ser Leu Glu Ile Val
            100                 105

<210> SEQ ID NO 2
<211> LENGTH: 107
<212> TYPE: PRT
<213> ORGANISM: Artificial Sequence
<220> FEATURE:
<223> OTHER INFORMATION: V-TIM1-2

<400> SEQUENCE: 2

Ser Val Lys Val Gly Gly Glu Ala Gly Pro Ser Val Thr Leu Pro Cys
1               5                   10                  15

His Tyr Ser Gly Ala Val Thr Ser Met Cys Trp Asn Arg Gly Ser Cys
            20                  25                  30

Ser Leu Phe Thr Cys Gln Asn Gly Ile Val Trp Thr Asn Gly Thr His
        35                  40                  45

Val Thr Tyr Arg Lys Asp Thr Arg Tyr Lys Leu Leu Gly Asp Leu Ser
    50                  55                  60

Arg Arg Asp Val Ser Leu Thr Ile Glu Asn Thr Ala Val Ser Asp Ser
65                  70                  75                  80

Gly Val Tyr Cys Cys Arg Val Glu His Arg Gly Trp Phe Asn Asp Met
                85                  90                  95

Lys Ile Thr Val Ser Leu Glu Ile Val Pro Pro
            100                 105

<210> SEQ ID NO 3
<211> LENGTH: 136
<212> TYPE: PRT
<213> ORGANISM: Artificial Sequence
<220> FEATURE:
<223> OTHER INFORMATION: V-CTLD-1
```

<400> SEQUENCE: 3

```
Glu Arg Leu Cys His Pro Cys Pro Trp Glu Trp Thr Phe Phe Gln Gly
1               5                   10                  15
Asn Cys Tyr Phe Met Ser Asn Ser Gln Arg Asn Trp His Asp Ser Ile
            20                  25                  30
Thr Ala Cys Lys Glu Val Gly Ala Gln Leu Val Val Ile Lys Ser Ala
        35                  40                  45
Glu Glu Gln Asn Phe Leu Gln Leu Gln Ser Ser Arg Ser Asn Arg Phe
    50                  55                  60
Thr Trp Met Gly Leu Ser Asp Leu Asn Gln Glu Gly Thr Trp Gln Trp
65                  70                  75                  80
Val Asp Gly Ser Pro Leu Leu Pro Ser Phe Lys Gln Tyr Trp Asn Arg
                85                  90                  95
Gly Glu Pro Asn Asn Val Gly Glu Glu Asp Cys Ala Glu Phe Ser Gly
            100                 105                 110
Asn Gly Trp Asn Asp Asp Lys Cys Asn Leu Ala Lys Phe Trp Ile Cys
        115                 120                 125
Lys Lys Ser Ala Ala Ser Cys Ser
    130                 135
```

<210> SEQ ID NO 4
<211> LENGTH: 130
<212> TYPE: PRT
<213> ORGANISM: Artificial Sequence
<220> FEATURE:
<223> OTHER INFORMATION: V-CTLD-2

<400> SEQUENCE: 4

```
His Pro Cys Pro Trp Glu Trp Thr Phe Phe Gln Gly Asn Cys Tyr Phe
1               5                   10                  15
Met Ser Asn Ser Gln Arg Asn Trp His Asp Ser Ile Thr Ala Cys Lys
            20                  25                  30
Glu Val Gly Ala Gln Leu Val Val Ile Lys Ser Ala Glu Glu Gln Asn
        35                  40                  45
Phe Leu Gln Leu Gln Ser Ser Arg Ser Asn Arg Phe Thr Trp Met Gly
    50                  55                  60
Leu Ser Asp Leu Asn Gln Glu Gly Thr Trp Gln Trp Val Asp Gly Ser
65                  70                  75                  80
Pro Leu Leu Pro Ser Phe Lys Gln Tyr Trp Asn Arg Gly Glu Pro Asn
                85                  90                  95
Asn Val Gly Glu Glu Asp Cys Ala Glu Phe Ser Gly Asn Gly Trp Asn
            100                 105                 110
Asp Asp Lys Cys Asn Leu Ala Lys Phe Trp Ile Cys Lys Lys Ser Ala
        115                 120                 125
Ala Ser
    130
```

<210> SEQ ID NO 5
<211> LENGTH: 343
<212> TYPE: PRT
<213> ORGANISM: Artificial Sequence
<220> FEATURE:
<223> OTHER INFORMATION: WT huIgG3 CH1-CH2-CH3

<400> SEQUENCE: 5

```
Ala Ser Thr Lys Gly Pro Ser Val Phe Pro Leu Ala Pro Cys Ser Arg
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Pro Glu
            100                 105                 110

Pro Lys Ser Cys Asp Thr Pro Pro Cys Pro Arg Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Gln Phe Lys Trp Tyr Val Asp
                165                 170                 175

Gly Val Glu Val His Asn Ala Lys Thr Lys Pro Arg Glu Glu Gln Tyr
            180                 185                 190

Asn Ser Thr Phe Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Thr Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Ser Gly Gln Pro Glu Asn Asn Tyr Asn
        275                 280                 285

Thr Thr Pro Pro Met Leu Asp Ser Asp Gly Ser Phe Phe Leu Tyr Ser
    290                 295                 300

Lys Leu Thr Val Asp Lys Ser Arg Trp Gln Gln Gly Asn Ile Phe Ser
305                 310                 315                 320

Cys Ser Val Met His Glu Ala Leu His Asn Arg Phe Thr Gln Lys Ser
                325                 330                 335

Leu Ser Leu Ser Pro Gly Lys
            340

<210> SEQ ID NO 6
<211> LENGTH: 29
<212> TYPE: PRT
<213> ORGANISM: Artificial Sequence
<220> FEATURE:
<223> OTHER INFORMATION: WT huIgG3 CH1-CH2-CH3 hinge region

<400> SEQUENCE: 6

Leu Lys Thr Pro Leu Gly Asp Thr Thr His Thr Pro Glu Pro Lys Ser
1               5                   10                  15

Cys Asp Thr Pro Pro Cys Pro Arg Cys Pro Ala Pro
            20                  25

<210> SEQ ID NO 7
<211> LENGTH: 327
<212> TYPE: PRT
<213> ORGANISM: Artificial Sequence
<220> FEATURE:
<223> OTHER INFORMATION: V-IGG3

<400> SEQUENCE: 7

```
Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Gln Phe Lys Trp Tyr Val Asp
145                 150                 155                 160

Gly Val Glu Val His Asn Ala Lys Thr Lys Pro Arg Glu Glu Gln Tyr
                165                 170                 175

Asn Ser Thr Phe Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Thr Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Ser Gly Gln Pro Glu Asn Asn Tyr Asn
            260                 265                 270

Thr Thr Pro Pro Met Leu Asp Ser Asp Gly Ser Phe Phe Leu Tyr Ser
        275                 280                 285

Lys Leu Thr Val Asp Lys Ser Arg Trp Gln Gln Gly Asn Ile Phe Ser
    290                 295                 300

Cys Ser Val Met His Glu Ala Leu His Asn Arg Phe Thr Gln Lys Ser
305                 310                 315                 320

Leu Ser Leu Ser Pro Gly Lys
                325
```

<210> SEQ ID NO 8
<211> LENGTH: 13
<212> TYPE: PRT
<213> ORGANISM: Artificial Sequence

```
<220> FEATURE:
<223> OTHER INFORMATION: IgG4 hinge with S228P

<400> SEQUENCE: 8

Ser Lys Tyr Gly Pro Pro Cys Pro Cys Pro Ala Pro
1               5                   10

<210> SEQ ID NO 9
<211> LENGTH: 242
<212> TYPE: PRT
<213> ORGANISM: Artificial Sequence
<220> FEATURE:
<223> OTHER INFORMATION: V-IGG3-Fc

<400> SEQUENCE: 9

Gly Gly Gly Gly Ser Gly Gly Gly Ser Gly Gly Gly Gly Ser Lys
1               5                   10                  15

Tyr Gly Pro Pro Cys Pro Pro Cys Pro Ala Pro Glu Leu Leu Gly Gly
                20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
50                  55                  60

Asp Pro Glu Val Gln Phe Lys Trp Tyr Val Asp Gly Val Glu Val His
65                  70                  75                  80

Asn Ala Lys Thr Lys Pro Arg Glu Glu Gln Tyr Asn Ser Thr Phe Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Thr Lys Gly Gln Pro Arg Glu Pro Gln Val Tyr
130                 135                 140

Thr Leu Pro Pro Ser Arg Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Ser Gly Gln Pro Glu Asn Asn Tyr Asn Thr Thr Pro Pro Met
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Ile Phe Ser Cys Ser Val Met His
210                 215                 220

Glu Ala Leu His Asn Arg Phe Thr Gln Lys Ser Leu Ser Leu Ser Pro
225                 230                 235                 240

Gly Lys

<210> SEQ ID NO 10
<211> LENGTH: 327
<212> TYPE: PRT
<213> ORGANISM: Artificial Sequence
<220> FEATURE:
<223> OTHER INFORMATION: V-IGG3-A with K409R

<400> SEQUENCE: 10

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
```

```
                    20                  25                  30
Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Leu Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser His Glu Asp Pro Glu Val Gln Phe Lys Trp Tyr Val Asp
145                 150                 155                 160

Gly Val Glu Val His Asn Ala Lys Thr Lys Pro Arg Glu Glu Gln Tyr
                165                 170                 175

Asn Ser Thr Phe Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Thr Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Ser Gly Gln Pro Glu Asn Asn Tyr Asn
            260                 265                 270

Thr Thr Pro Pro Met Leu Asp Ser Asp Gly Ser Phe Phe Leu Tyr Ser
        275                 280                 285

Arg Leu Thr Val Asp Lys Ser Arg Trp Gln Gln Gly Asn Ile Phe Ser
    290                 295                 300

Cys Ser Val Met His Glu Ala Leu His Asn Arg Phe Thr Gln Lys Ser
305                 310                 315                 320

Leu Ser Leu Ser Pro Gly Lys
                325

<210> SEQ ID NO 11
<211> LENGTH: 242
<212> TYPE: PRT
<213> ORGANISM: Artificial Sequence
<220> FEATURE:
<223> OTHER INFORMATION: V-IGG3-A-Fc

<400> SEQUENCE: 11

Gly Gly Gly Gly Ser Gly Gly Gly Ser Gly Gly Gly Gly Ser Lys
1               5                   10                  15

Tyr Gly Pro Pro Cys Pro Pro Cys Pro Ala Pro Glu Leu Leu Gly Gly
                20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
```

```
                50                  55                  60
Asp Pro Glu Val Gln Phe Lys Trp Tyr Val Asp Gly Val Glu Val His
 65                  70                  75                  80

Asn Ala Lys Thr Lys Pro Arg Glu Glu Gln Tyr Asn Ser Thr Phe Arg
                 85                  90                  95

Val Val Ser Val Leu Thr Val Leu His Gln Asp Trp Leu Asn Gly Lys
                100                 105                 110

Glu Tyr Lys Cys Lys Val Ser Asn Lys Ala Leu Pro Ala Pro Ile Glu
                115                 120                 125

Lys Thr Ile Ser Lys Thr Lys Gly Gln Pro Arg Glu Pro Gln Val Tyr
                130                 135                 140

Thr Leu Pro Pro Ser Arg Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Ser Gly Gln Pro Glu Asn Asn Tyr Asn Thr Thr Pro Pro Met
                180                 185                 190

Leu Asp Ser Asp Gly Ser Phe Phe Leu Tyr Ser Arg Leu Thr Val Asp
                195                 200                 205

Lys Ser Arg Trp Gln Gln Gly Asn Ile Phe Ser Cys Ser Val Met His
                210                 215                 220

Glu Ala Leu His Asn Arg Phe Thr Gln Lys Ser Leu Ser Leu Ser Pro
225                 230                 235                 240

Gly Lys

<210> SEQ ID NO 12
<211> LENGTH: 327
<212> TYPE: PRT
<213> ORGANISM: Artificial Sequence
<220> FEATURE:
<223> OTHER INFORMATION: V-IGG3-B

<400> SEQUENCE: 12

Ala Ser Thr Lys Gly Pro Ser Val Phe Pro Leu Ala Pro Cys Ser Arg
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
             50                  55                  60

Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Leu Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser His Glu Asp Pro Glu Val Gln Phe Lys Trp Tyr Val Asp
145                 150                 155                 160

Gly Val Glu Val His Asn Ala Lys Thr Lys Pro Arg Glu Glu Gln Tyr
                165                 170                 175
```

```
Asn Ser Thr Phe Arg Val Val Ser Val Leu Thr Val Leu His Gln Asp
                180                 185                 190

Trp Leu Asn Gly Lys Glu Tyr Lys Cys Lys Val Ser Asn Lys Ala Leu
            195                 200                 205

Pro Ala Pro Ile Glu Lys Thr Ile Ser Lys Thr Lys Gly Gln Pro Arg
        210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Ser Gly Gln Pro Glu Asn Asn Tyr Asn
            260                 265                 270

Thr Thr Pro Pro Met Leu Asp Ser Asp Gly Ser Phe Leu Leu Tyr Ser
        275                 280                 285

Lys Leu Thr Val Asp Lys Ser Arg Trp Gln Gln Gly Asn Ile Phe Ser
    290                 295                 300

Cys Ser Val Met His Glu Ala Leu His Asn Arg Phe Thr Gln Lys Ser
305                 310                 315                 320

Leu Ser Leu Ser Pro Gly Lys
                325

<210> SEQ ID NO 13
<211> LENGTH: 242
<212> TYPE: PRT
<213> ORGANISM: Artificial Sequence
<220> FEATURE:
<223> OTHER INFORMATION: V-IGG3-B-Fc

<400> SEQUENCE: 13

Gly Gly Gly Gly Ser Gly Gly Gly Ser Gly Gly Gly Ser Lys
1               5                   10                  15

Tyr Gly Pro Pro Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Gln Phe Lys Trp Tyr Val Asp Gly Val Glu Val His
65                  70                  75                  80

Asn Ala Lys Thr Lys Pro Arg Glu Glu Gln Tyr Asn Ser Thr Phe Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Thr Lys Gly Gln Pro Arg Glu Pro Gln Val Tyr
    130                 135                 140

Thr Leu Pro Pro Ser Arg Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Ser Gly Gln Pro Glu Asn Asn Tyr Asn Thr Thr Pro Pro Met
            180                 185                 190

Leu Asp Ser Asp Gly Ser Phe Leu Leu Tyr Ser Lys Leu Thr Val Asp
        195                 200                 205
```

```
Lys Ser Arg Trp Gln Gln Gly Asn Ile Phe Ser Cys Ser Val Met His
    210                 215                 220

Glu Ala Leu His Asn Arg Phe Thr Gln Lys Ser Leu Ser Leu Ser Pro
225                 230                 235                 240

Gly Lys

<210> SEQ ID NO 14
<211> LENGTH: 242
<212> TYPE: PRT
<213> ORGANISM: Artificial Sequence
<220> FEATURE:
<223> OTHER INFORMATION: V-IGG4-A-Fc

<400> SEQUENCE: 14

Gly Gly Gly Gly Ser Gly Gly Gly Ser Gly Gly Gly Gly Ser Lys
1               5                   10                  15

Tyr Gly Pro Pro Cys Pro Pro Cys Pro Ala Pro Glu Ala Ala Gly Gly
                20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser Gln Glu
50                  55                  60

Asp Pro Glu Val Gln Phe Asn Trp Tyr Val Asp Gly Val Glu Val His
65                  70                  75                  80

Asn Ala Lys Thr Lys Pro Arg Glu Glu Gln Phe Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Ala Val Ser Asn Lys Gly Leu Pro Ser Ser Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Gln Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Arg Leu Thr Val Asp
        195                 200                 205

Lys Ser Arg Trp Gln Glu Gly Asn Val Phe Ser Cys Ser Val Met His
    210                 215                 220

Glu Ala Leu His Asn His Tyr Thr Gln Lys Ser Leu Ser Leu Ser Leu
225                 230                 235                 240

Gly Lys

<210> SEQ ID NO 15
<211> LENGTH: 241
<212> TYPE: PRT
<213> ORGANISM: Artificial Sequence
<220> FEATURE:
<223> OTHER INFORMATION: V-IGG2-A-Fc

<400> SEQUENCE: 15

Gly Gly Gly Gly Ser Gly Gly Gly Ser Gly Gly Gly Gly Ser Asp
1               5                   10                  15
```

Lys Thr His Thr Cys Pro Pro Cys Pro Ala Pro Ala Gly Pro
                20                  25                  30

Ser Val Phe Leu Phe Pro Pro Lys Pro Lys Asp Thr Leu Met Ile Ser
                35                  40                  45

Arg Thr Pro Glu Val Thr Cys Val Val Val Asp Val Ser His Glu Asp
 50                  55                  60

Pro Glu Val Gln Phe Asn Trp Tyr Val Asp Gly Val Glu Val His Asn
65                  70                  75                  80

Ala Lys Thr Lys Pro Arg Glu Glu Gln Phe Asn Ser Thr Phe Arg Val
                85                  90                  95

Val Ser Val Leu Thr Val Val His Gln Asp Trp Leu Asn Gly Lys Glu
                100                 105                 110

Tyr Lys Cys Ala Val Ser Asn Lys Gly Leu Pro Ala Pro Ile Glu Lys
                115                 120                 125

Thr Ile Ser Lys Thr Lys Gly Gln Pro Arg Glu Pro Gln Val Tyr Thr
                130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ser Val Glu Trp Glu
                165                 170                 175

Ser Asn Gly Gln Pro Glu Asn Asn Tyr Lys Thr Thr Pro Pro Met Leu
                180                 185                 190

Asp Ser Asp Gly Ser Phe Phe Leu Tyr Ser Arg Leu Thr Val Asp Lys
                195                 200                 205

Ser Arg Trp Gln Gln Gly Asn Val Phe Ser Cys Ser Val Met His Glu
                210                 215                 220

Ala Leu His Asn His Tyr Thr Gln Lys Ser Leu Ser Leu Ser Pro Gly
225                 230                 235                 240

Lys

<210> SEQ ID NO 16
<211> LENGTH: 242
<212> TYPE: PRT
<213> ORGANISM: Artificial Sequence
<220> FEATURE:
<223> OTHER INFORMATION: V-IGG4-B-Fc

<400> SEQUENCE: 16

Gly Gly Gly Gly Ser Gly Gly Gly Gly Ser Gly Gly Gly Gly Ser Lys
1               5                   10                  15

Tyr Gly Pro Pro Cys Pro Pro Cys Pro Ala Pro Glu Ala Ala Gly Gly
                20                  25                  30

Pro Ser Val Phe Leu Phe Pro Pro Lys Pro Lys Asp Thr Leu Met Ile
                35                  40                  45

Ser Arg Thr Pro Glu Val Thr Cys Val Val Val Asp Val Ser Gln Glu
 50                  55                  60

Asp Pro Glu Val Gln Phe Asn Trp Tyr Val Asp Gly Val Glu Val His
65                  70                  75                  80

Asn Ala Lys Thr Lys Pro Arg Glu Glu Gln Phe Asn Ser Thr Tyr Arg
                85                  90                  95

Val Val Ser Val Leu Thr Val Leu His Gln Asp Trp Leu Asn Gly Lys
                100                 105                 110

Glu Tyr Lys Cys Ala Val Ser Asn Lys Gly Leu Pro Ser Ser Ile Glu
                115                 120                 125

Lys Thr Ile Ser Lys Ala Lys Gly Gln Pro Arg Glu Pro Gln Val Tyr

```
                130                 135                 140
Thr Leu Pro Pro Ser Gln Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
                180                 185                 190

Leu Asp Ser Asp Gly Ser Phe Leu Leu Tyr Ser Lys Leu Thr Val Asp
                195                 200                 205

Lys Ser Arg Trp Gln Glu Gly Asn Val Phe Ser Cys Ser Val Met His
            210                 215                 220

Glu Ala Leu His Asn His Tyr Thr Gln Lys Ser Leu Ser Leu Ser Leu
225                 230                 235                 240

Gly Lys
```

<210> SEQ ID NO 17
<211> LENGTH: 241
<212> TYPE: PRT
<213> ORGANISM: Artificial Sequence
<220> FEATURE:
<223> OTHER INFORMATION: V-IGG2-B-Fc

<400> SEQUENCE: 17

```
Gly Gly Gly Gly Ser Gly Gly Gly Ser Gly Gly Gly Gly Ser Asp
1               5                   10                  15

Lys Thr His Thr Cys Pro Pro Cys Pro Ala Pro Ala Ala Gly Pro
                20                  25                  30

Ser Val Phe Leu Phe Pro Pro Lys Pro Lys Asp Thr Leu Met Ile Ser
                35                  40                  45

Arg Thr Pro Glu Val Thr Cys Val Val Val Asp Val Ser His Glu Asp
            50                  55                  60

Pro Glu Val Gln Phe Asn Trp Tyr Val Asp Gly Val Glu Val His Asn
65                  70                  75                  80

Ala Lys Thr Lys Pro Arg Glu Glu Gln Phe Asn Ser Thr Phe Arg Val
                85                  90                  95

Val Ser Val Leu Thr Val Val His Gln Asp Trp Leu Asn Gly Lys Glu
                100                 105                 110

Tyr Lys Cys Ala Val Ser Asn Lys Gly Leu Pro Ala Pro Ile Glu Lys
            115                 120                 125

Thr Ile Ser Lys Thr Lys Gly Gln Pro Arg Glu Pro Gln Val Tyr Thr
130                 135                 140

Leu Pro Pro Ser Arg Glu Glu Met Thr Lys Asn Gln Val Ser Leu Thr
145                 150                 155                 160

Cys Leu Val Lys Gly Phe Tyr Pro Ser Asp Ile Ser Val Glu Trp Glu
                165                 170                 175

Ser Asn Gly Gln Pro Glu Asn Asn Tyr Lys Thr Thr Pro Pro Met Leu
                180                 185                 190

Asp Ser Asp Gly Ser Phe Leu Leu Tyr Ser Lys Leu Thr Val Asp Lys
            195                 200                 205

Ser Arg Trp Gln Gln Gly Asn Val Phe Ser Cys Ser Val Met His Glu
            210                 215                 220

Ala Leu His Asn His Tyr Thr Gln Lys Ser Leu Ser Leu Ser Pro Gly
225                 230                 235                 240

Lys
```

<210> SEQ ID NO 18
<211> LENGTH: 255
<212> TYPE: PRT
<213> ORGANISM: Artificial Sequence
<220> FEATURE:
<223> OTHER INFORMATION: VCD3-H1L1

<400> SEQUENCE: 18

```
Gln Val Gln Leu Val Gln Ser Gly Gly Gly Val Val Gln Pro Gly Arg
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Val
        35                  40                  45

Gly Tyr Ile Asn Pro Ser Arg Gly Tyr Thr Asn Tyr Asn Asp Ser Val
    50                  55                  60

Lys Gly Arg Phe Thr Ile Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Gln Ala Ser Ser
                165                 170                 175

Ser Val Ser Tyr Met Asn Trp Tyr Gln Gln Lys Pro Gly Lys Ala Pro
            180                 185                 190

Lys Arg Trp Ile Tyr Asp Thr Ser Lys Leu Ala Ser Gly Val Pro Ser
        195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Gln Gly Thr Lys Leu Glu Ile Lys
                245                 250                 255
```

<210> SEQ ID NO 19
<211> LENGTH: 255
<212> TYPE: PRT
<213> ORGANISM: Artificial Sequence
<220> FEATURE:
<223> OTHER INFORMATION: VCD3-H1L1-DS

<400> SEQUENCE: 19

```
Gln Val Gln Leu Val Gln Ser Gly Gly Gly Val Val Gln Pro Gly Arg
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Cys Leu Glu Trp Val
        35                  40                  45

Gly Tyr Ile Asn Pro Ser Arg Gly Tyr Thr Asn Tyr Asn Asp Ser Val
    50                  55                  60
```

Lys Gly Arg Phe Thr Ile Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Gln Ala Ser Ser
                165                 170                 175

Ser Val Ser Tyr Met Asn Trp Tyr Gln Gln Lys Pro Gly Lys Ala Pro
            180                 185                 190

Lys Arg Trp Ile Tyr Asp Thr Ser Lys Leu Ala Ser Gly Val Pro Ser
            195                 200                 205

Arg Phe Ser Gly Ser Gly Ser Gly Thr Asp Tyr Thr Phe Thr Ile Ser
210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Cys Gly Thr Lys Leu Glu Ile Lys
                245                 250                 255

<210> SEQ ID NO 20
<211> LENGTH: 255
<212> TYPE: PRT
<213> ORGANISM: Artificial Sequence
<220> FEATURE:
<223> OTHER INFORMATION: VCD3-H1L2

<400> SEQUENCE: 20

Gln Val Gln Leu Val Gln Ser Gly Gly Gly Val Val Gln Pro Gly Arg
1               5                   10                  15

Ser Leu Arg Leu Ser Cys Ala Ala Ser Gly Tyr Thr Phe Thr Arg Tyr
                20                  25                  30

Thr Met His Trp Val Arg Gln Ala Pro Gly Lys Gly Leu Glu Trp Val
            35                  40                  45

Gly Tyr Ile Asn Pro Ser Arg Gly Tyr Thr Asn Tyr Asn Asp Ser Val
    50                  55                  60

Lys Gly Arg Phe Thr Ile Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

```
Ser Val Ser Tyr Met Asn Trp Tyr Gln Gln Lys Pro Gly Gln Ala Pro
            180                 185                 190

Arg Arg Leu Ile Tyr Asp Thr Ser Lys Arg Ala Thr Gly Ile Pro Ala
            195                 200                 205

Arg Phe Ser Gly Ser Gly Ser Gly Thr Asp Tyr Thr Leu Thr Ile Ser
210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
            245                 250                 255

<210> SEQ ID NO 21
<211> LENGTH: 255
<212> TYPE: PRT
<213> ORGANISM: Artificial Sequence
<220> FEATURE:
<223> OTHER INFORMATION: VCD3-H1L2-DS

<400> SEQUENCE: 21

Gln Val Gln Leu Val Gln Ser Gly Gly Gly Val Val Gln Pro Gly Arg
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Cys Leu Glu Trp Val
        35                  40                  45

Gly Tyr Ile Asn Pro Ser Arg Gly Tyr Thr Asn Tyr Asn Asp Ser Val
    50                  55                  60

Lys Gly Arg Phe Thr Ile Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
            165                 170                 175

Ser Val Ser Tyr Met Asn Trp Tyr Gln Gln Lys Pro Gly Gln Ala Pro
            180                 185                 190

Arg Arg Leu Ile Tyr Asp Thr Ser Lys Arg Ala Thr Gly Ile Pro Ala
            195                 200                 205

Arg Phe Ser Gly Ser Gly Ser Gly Thr Asp Tyr Thr Leu Thr Ile Ser
210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Cys Gly Thr Lys Leu Glu Ile Lys
            245                 250                 255

<210> SEQ ID NO 22
<211> LENGTH: 255
<212> TYPE: PRT
<213> ORGANISM: Artificial Sequence
```

<220> FEATURE:
<223> OTHER INFORMATION: VCD3-H1L3

<400> SEQUENCE: 22

Gln Val Gln Leu Val Gln Ser Gly Gly Gly Val Val Gln Pro Gly Arg
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Gly Leu Glu Trp Val
        35                  40                  45

Gly Tyr Ile Asn Pro Ser Arg Gly Tyr Thr Asn Tyr Asn Asp Ser Val
50                  55                  60

Lys Gly Arg Phe Thr Ile Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Glu Ile Gln Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Trp Ile Tyr Asp Thr Ser Lys Leu Ala Thr Gly Ile Pro Ala
        195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
                245                 250                 255

<210> SEQ ID NO 23
<211> LENGTH: 255
<212> TYPE: PRT
<213> ORGANISM: Artificial Sequence
<220> FEATURE:
<223> OTHER INFORMATION: VCD3-H1L3-DS

<400> SEQUENCE: 23

Gln Val Gln Leu Val Gln Ser Gly Gly Gly Val Val Gln Pro Gly Arg
1               5                   10                  15

Ser Leu Arg Leu Ser Cys Ala Ala Ser Gly Tyr Thr Phe Thr Arg Tyr
            20                  25                  30

Thr Met His Trp Val Arg Gln Ala Pro Gly Lys Cys Leu Glu Trp Val
        35                  40                  45

Gly Tyr Ile Asn Pro Ser Arg Gly Tyr Thr Asn Tyr Asn Asp Ser Val
50                  55                  60

Lys Gly Arg Phe Thr Ile Ser Thr Asp Lys Ser Lys Asn Thr Ala Tyr
65                  70                  75                  80

Leu Gln Met Asn Ser Leu Arg Ala Glu Asp Thr Ala Val Tyr Tyr Cys

```
                        85                  90                  95
Ala Arg Tyr Tyr Asp Asp His Tyr Ser Leu Asp Tyr Trp Gly Gln Gly
                100                 105                 110

Thr Thr Val Thr Val Ser Ser Gly Gly Gly Ser Gly Gly Gly Gly
        115                 120                 125

Ser Gly Gly Gly Ser Gly Gly Gly Ser Gly Gly Gly Ser
    130                 135                 140

Gly Gly Gly Gly Ser Glu Ile Gln Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
                180                 185                 190

Arg Arg Trp Ile Tyr Asp Thr Ser Lys Leu Ala Thr Gly Ile Pro Ala
                195                 200                 205

Arg Phe Ser Gly Ser Gly Ser Gly Thr Asp Tyr Thr Leu Thr Ile Ser
        210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Cys Gly Thr Lys Leu Glu Ile Lys
                245                 250                 255
```

<210> SEQ ID NO 24
<211> LENGTH: 255
<212> TYPE: PRT
<213> ORGANISM: Artificial Sequence
<220> FEATURE:
<223> OTHER INFORMATION: VCD3-H2L1

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Met
            35                  40                  45

Gly Tyr Ile Asn Pro Ser Arg Gly Tyr Thr Asn Tyr Asn Gln Lys Phe
        50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
                100                 105                 110

Thr Thr Val Thr Val Ser Ser Gly Gly Gly Ser Gly Gly Gly Gly
        115                 120                 125

Ser Gly Gly Gly Gly Ser Gly Gly Gly Ser Gly Gly Gly Ser
    130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Gln Ala Ser Ser
                165                 170                 175

Ser Val Ser Tyr Met Asn Trp Tyr Gln Gln Lys Pro Gly Lys Ala Pro
                180                 185                 190

Lys Arg Trp Ile Tyr Asp Thr Ser Lys Leu Ala Ser Gly Val Pro Ser
```

```
                    195                 200                 205
Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Gln Gly Thr Lys Leu Glu Ile Lys
                245                 250                 255

<210> SEQ ID NO 25
<211> LENGTH: 255
<212> TYPE: PRT
<213> ORGANISM: Artificial Sequence
<220> FEATURE:
<223> OTHER INFORMATION: VCD3-H2L1-DS

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Cys Leu Glu Trp Met
            35                  40                  45

Gly Tyr Ile Asn Pro Ser Arg Gly Tyr Thr Asn Tyr Asn Gln Lys Phe
        50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
                100                 105                 110

Thr Thr Val Thr Val Ser Ser Gly Gly Gly Ser Gly Gly Gly Gly
            115                 120                 125

Ser Gly Gly Gly Gly Ser Gly Gly Gly Gly Ser Gly Gly Gly Gly Ser
        130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Gln Ala Ser Ser
                165                 170                 175

Ser Val Ser Tyr Met Asn Trp Tyr Gln Gln Lys Pro Gly Lys Ala Pro
                180                 185                 190

Lys Arg Trp Ile Tyr Asp Thr Ser Lys Leu Ala Ser Gly Val Pro Ser
                195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Cys Gly Thr Lys Leu Glu Ile Lys
                245                 250                 255

<210> SEQ ID NO 26
<211> LENGTH: 255
<212> TYPE: PRT
<213> ORGANISM: Artificial Sequence
<220> FEATURE:
<223> OTHER INFORMATION: VCD3-H2L2

<400> SEQUENCE: 26
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
            165                 170                 175

Ser Val Ser Tyr Met Asn Trp Tyr Gln Gln Lys Pro Gly Gln Ala Pro
        180                 185                 190

Arg Arg Leu Ile Tyr Asp Thr Ser Lys Arg Ala Thr Gly Ile Pro Ala
    195                 200                 205

Arg Phe Ser Gly Ser Gly Ser Gly Thr Asp Tyr Thr Leu Thr Ile Ser
210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
            245                 250                 255

<210> SEQ ID NO 27
<211> LENGTH: 255
<212> TYPE: PRT
<213> ORGANISM: Artificial Sequence
<220> FEATURE:
<223> OTHER INFORMATION: VCD3-H2L2-DS

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

```
Thr Thr Val Thr Val Ser Ser Gly Gly Gly Ser Gly Gly Gly
            115                 120                 125

Ser Gly Gly Gly Ser Gly Gly Gly Ser Gly Gly Gly Ser
    130                 135                 140

Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Leu Ile Tyr Asp Thr Ser Lys Arg Ala Thr Gly Ile Pro Ala
            195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Cys Gly Thr Lys Leu Glu Ile Lys
                245                 250                 255
```

<210> SEQ ID NO 28
<211> LENGTH: 255
<212> TYPE: PRT
<213> ORGANISM: Artificial Sequence
<220> FEATURE:
<223> OTHER INFORMATION: VCD3-H2L3

<400> SEQUENCE: 28

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gly Gly Gly Ser Gly Gly Gly Ser
    130                 135                 140

Gly Gly Gly Ser Glu Ile Gln Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Trp Ile Tyr Asp Thr Ser Lys Leu Ala Thr Gly Ile Pro Ala
            195                 200                 205

Arg Phe Ser Gly Ser Gly Ser Gly Thr Asp Tyr Thr Leu Thr Ile Ser
    210                 215                 220
```

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
            245                 250                 255

<210> SEQ ID NO 29
<211> LENGTH: 255
<212> TYPE: PRT
<213> ORGANISM: Artificial Sequence
<220> FEATURE:
<223> OTHER INFORMATION: VCD3-H2L3-DS

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Glu Ile Gln Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Trp Ile Tyr Asp Thr Ser Lys Leu Ala Thr Gly Ile Pro Ala
        195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Cys Gly Thr Lys Leu Glu Ile Lys
            245                 250                 255

<210> SEQ ID NO 30
<211> LENGTH: 255
<212> TYPE: PRT
<213> ORGANISM: Artificial Sequence
<220> FEATURE:
<223> OTHER INFORMATION: VCD3-H3L1

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

```
Thr Met His Trp Val Arg Gln Ser Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Gly Gly Gly Ser Gly Gly Gly Gly
        115                 120                 125

Ser Gly Gly Gly Gly Ser Gly Gly Gly Gly Ser Gly Gly Gly Gly Ser
130                 135                 140

Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Gln Ala Ser Ser
                165                 170                 175

Ser Val Ser Tyr Met Asn Trp Tyr Gln Gln Lys Pro Gly Lys Ala Pro
            180                 185                 190

Lys Arg Trp Ile Tyr Asp Thr Ser Lys Leu Ala Ser Gly Val Pro Ser
        195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Gln Gly Thr Lys Leu Glu Ile Lys
                245                 250                 255
```

<210> SEQ ID NO 31
<211> LENGTH: 255
<212> TYPE: PRT
<213> ORGANISM: Artificial Sequence
<220> FEATURE:
<223> OTHER INFORMATION: VCD3-H3L1-DS

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ser Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gly Gly Gly Gly Ser Gly Gly Gly Gly Ser
130                 135                 140
```

```
Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Gln Ala Ser Ser
                165                 170                 175

Ser Val Ser Tyr Met Asn Trp Tyr Gln Gln Lys Pro Gly Lys Ala Pro
            180                 185                 190

Lys Arg Trp Ile Tyr Asp Thr Ser Lys Leu Ala Ser Gly Val Pro Ser
        195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Cys Gly Thr Lys Leu Glu Ile Lys
                245                 250                 255

<210> SEQ ID NO 32
<211> LENGTH: 255
<212> TYPE: PRT
<213> ORGANISM: Artificial Sequence
<220> FEATURE:
<223> OTHER INFORMATION: VCD3-H3L2

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ser Pro Gly Gln Gly Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Leu Ile Tyr Asp Thr Ser Lys Arg Ala Thr Gly Ile Pro Ala
        195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
                245                 250                 255
```

<210> SEQ ID NO 33
<211> LENGTH: 255
<212> TYPE: PRT
<213> ORGANISM: Artificial Sequence
<220> FEATURE:
<223> OTHER INFORMATION: VCD3-H3L2-DS

<400> SEQUENCE: 33

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ser Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Gln Gly Arg Val Thr Met Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Glu Ile Val Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Leu Ile Tyr Asp Thr Ser Lys Arg Ala Thr Gly Ile Pro Ala
        195                 200                 205

Arg Phe Ser Gly Ser Gly Ser Gly Thr Asp Tyr Thr Leu Thr Ile Ser
    210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Cys Gly Thr Lys Leu Glu Ile Lys
                245                 250                 255
```

<210> SEQ ID NO 34
<211> LENGTH: 255
<212> TYPE: PRT
<213> ORGANISM: Artificial Sequence
<220> FEATURE:
<223> OTHER INFORMATION: VCD3-H3L3

<400> SEQUENCE: 34

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ser Pro Gly Gln Gly Leu Glu Trp Met
        35                  40                  45

Gly Tyr Ile Asn Pro Ser Arg Gly Tyr Thr Asn Tyr Asn Gln Lys Phe
```

```
            50                  55                  60
Gln Gly Arg Val Thr Met Thr Thr Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gly Gly Gly Gly Ser Gly Gly Gly Ser
130                 135                 140

Gly Gly Gly Gly Ser Glu Ile Gln Leu Thr Gln Ser Pro Ala Thr Leu
145                 150                 155                 160

Ser Leu Ser Pro Gly Glu Arg Ala Thr Leu Ser Cys Arg Ala Ser Ser
                165                 170                 175

Ser Val Ser Tyr Met Asn Trp Tyr Gln Gln Lys Pro Gly Gln Ala Pro
            180                 185                 190

Arg Arg Trp Ile Tyr Asp Thr Ser Lys Leu Ala Thr Gly Ile Pro Ala
        195                 200                 205

Arg Phe Ser Gly Ser Gly Ser Gly Thr Asp Tyr Thr Leu Thr Ile Ser
210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Gln Gly Thr Lys Leu Glu Ile Lys
                245                 250                 255

<210> SEQ ID NO 35
<211> LENGTH: 255
<212> TYPE: PRT
<213> ORGANISM: Artificial Sequence
<220> FEATURE:
<223> OTHER INFORMATION: VCD3-H3L3-DS

<400> SEQUENCE: 35

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Arg Tyr
             20                  25                  30

Thr Met His Trp Val Arg Gln Ser Pro Gly Gln Cys Leu Glu Trp Met
         35                  40                  45

Gly Tyr Ile Asn Pro Ser Arg Gly Tyr Thr Asn Tyr Asn Gln Lys Phe
     50                  55                  60

Gln Gly Arg Val Thr Met Thr Thr Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Tyr Asp Asp His Tyr Ser Leu Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
130                 135                 140

Gly Gly Gly Gly Ser Glu Ile Gln Leu Thr Gln Ser Pro Ala Thr Leu
145                 150                 155                 160

Ser Leu Ser Pro Gly Glu Arg Ala Thr Leu Ser Cys Arg Ala Ser Ser
```

```
                165                 170                 175
Ser Val Ser Tyr Met Asn Trp Tyr Gln Gln Lys Pro Gly Gln Ala Pro
            180                 185                 190

Arg Arg Trp Ile Tyr Asp Thr Ser Lys Leu Ala Thr Gly Ile Pro Ala
            195                 200                 205

Arg Phe Ser Gly Ser Gly Ser Gly Thr Asp Tyr Thr Leu Thr Ile Ser
        210                 215                 220

Ser Leu Glu Pro Glu Asp Ala Ala Val Tyr Tyr Cys Gln Gln Trp Ser
225                 230                 235                 240

Ser Asn Pro Phe Thr Phe Gly Cys Gly Thr Lys Leu Glu Ile Lys
                245                 250                 255

<210> SEQ ID NO 36
<211> LENGTH: 327
<212> TYPE: PRT
<213> ORGANISM: Artificial Sequence
<220> FEATURE:
<223> OTHER INFORMATION: V-IGG4-A

<400> SEQUENCE: 36

Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Ala Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
```

```
                    275                 280                 285
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 37
<211> LENGTH: 327
<212> TYPE: PRT
<213> ORGANISM: Artificial Sequence
<220> FEATURE:
<223> OTHER INFORMATION: V-IGG4-ADC-A

<400> SEQUENCE: 37

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Ala Val Ser Asn Lys Gly Leu
        195                 200                 205

Pro Ser Ser Ile Glu Lys Thr Ile Ser Lys Cys Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
```

Leu Ser Leu Ser Leu Gly Lys
            325

<210> SEQ ID NO 38
<211> LENGTH: 242
<212> TYPE: PRT
<213> ORGANISM: Artificial Sequence
<220> FEATURE:
<223> OTHER INFORMATION: V-IGG4-ADC-A -Fc

<400> SEQUENCE: 38

Gly Gly Gly Gly Ser Gly Gly Gly Ser Gly Gly Gly Ser Lys
1               5                   10                  15

Tyr Gly Pro Pro Cys Pro Pro Cys Pro Ala Pro Glu Ala Ala Gly Gly
            20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser Gln Glu
    50                  55                  60

Asp Pro Glu Val Gln Phe Asn Trp Tyr Val Asp Gly Val Glu Val His
65                  70                  75                  80

Asn Ala Lys Thr Lys Pro Arg Glu Glu Gln Phe Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Ala Val Ser Asn Lys Gly Leu Pro Ser Ser Ile Glu
        115                 120                 125

Lys Thr Ile Ser Lys Cys Lys Gly Gln Pro Arg Glu Pro Gln Val Tyr
    130                 135                 140

Thr Leu Pro Pro Ser Gln Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Arg Leu Thr Val Asp
        195                 200                 205

Lys Ser Arg Trp Gln Glu Gly Asn Val Phe Ser Cys Ser Val Met His
    210                 215                 220

Glu Ala Leu His Asn His Tyr Thr Gln Lys Ser Leu Ser Leu Ser Leu
225                 230                 235                 240

Gly Lys

<210> SEQ ID NO 39
<211> LENGTH: 327
<212> TYPE: PRT
<213> ORGANISM: Artificial Sequence
<220> FEATURE:
<223> OTHER INFORMATION: V-IGG4-ADC-B

<400> SEQUENCE: 39

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                    35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Ala Ala Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Ala Val Ser Asn Lys Gly Leu
        195                 200                 205
Pro Ser Ser Ile Glu Lys Thr Ile Ser Lys Cys Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Leu Leu Tyr Ser
        275                 280                 285
Lys Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 40
<211> LENGTH: 242
<212> TYPE: PRT
<213> ORGANISM: Artificial Sequence
<220> FEATURE:
<223> OTHER INFORMATION: V-IGG4-ADC-B-Fc

<400> SEQUENCE: 40

Gly Gly Gly Gly Ser Gly Gly Gly Ser Gly Gly Gly Ser Lys
1               5                   10                  15
Tyr Gly Pro Pro Cys Pro Pro Cys Pro Ala Pro Glu Ala Ala Gly Gly
                20                  25                  30
Pro Ser Val Phe Leu Phe Pro Pro Lys Pro Lys Asp Thr Leu Met Ile
            35                  40                  45
Ser Arg Thr Pro Glu Val Thr Cys Val Val Val Asp Val Ser Gln Glu
50                  55                  60
Asp Pro Glu Val Gln Phe Asn Trp Tyr Val Asp Gly Val Glu Val His
```

```
              65                  70                  75                  80
Asn Ala Lys Thr Lys Pro Arg Glu Glu Gln Phe Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Ala Val Ser Asn Lys Gly Leu Pro Ser Ser Ile Glu
        115                 120                 125

Lys Thr Ile Ser Lys Cys Lys Gly Gln Pro Arg Glu Pro Gln Val Tyr
    130                 135                 140

Thr Leu Pro Pro Ser Gln Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Leu Leu Tyr Ser Lys Leu Thr Val Asp
        195                 200                 205

Lys Ser Arg Trp Gln Glu Gly Asn Val Phe Ser Cys Ser Val Met His
    210                 215                 220

Glu Ala Leu His Asn His Tyr Thr Gln Lys Ser Leu Ser Leu Ser Leu
225                 230                 235                 240

Gly Lys

<210> SEQ ID NO 41
<211> LENGTH: 15
<212> TYPE: PRT
<213> ORGANISM: Artificial Sequence
<220> FEATURE:
<223> OTHER INFORMATION: Linker sequence

<400> SEQUENCE: 41

Gly Gly Gly Gly Ser Gly Gly Gly Ser Gly Gly Gly Gly Ser
1               5                   10                  15

<210> SEQ ID NO 42
<211> LENGTH: 330
<212> TYPE: PRT
<213> ORGANISM: Artificial Sequence
<220> FEATURE:
<223> OTHER INFORMATION: V-IGG3-C

<400> SEQUENCE: 42

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Gly Asp Thr Thr His Thr Cys Pro Arg Cys
            100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Phe Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Thr Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
            260                 265                 270

Asn Tyr Asn Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 43
<211> LENGTH: 245
<212> TYPE: PRT
<213> ORGANISM: Artificial Sequence
<220> FEATURE:
<223> OTHER INFORMATION: V-IGG3-C-Fc

<400> SEQUENCE: 43

Gly Gly Gly Gly Ser Gly Gly Gly Ser Gly Gly Gly Gly Ser Lys
1               5                   10                  15

Thr Gly Asp Thr Thr His Thr Cys Pro Arg Cys Pro Ala Pro Glu Leu
                20                  25                  30

Leu Gly Gly Pro Ser Val Phe Leu Phe Pro Pro Lys Pro Lys Asp Thr
            35                  40                  45

Leu Met Ile Ser Arg Thr Pro Glu Val Thr Cys Val Val Val Asp Val
        50                  55                  60

Ser His Glu Asp Pro Glu Val Gln Phe Lys Trp Tyr Val Asp Gly Val
65                  70                  75                  80

Glu Val His Asn Ala Lys Thr Lys Pro Arg Glu Glu Gln Tyr Asn Ser
                85                  90                  95

Thr Phe Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Thr Lys Gly Gln Pro Arg Glu Pro
    130                 135                 140

Gln Val Tyr Thr Leu Pro Pro Ser Arg Glu Glu Met Thr Lys Asn Gln
```

```
            145                 150                 155                 160
Val Ser Leu Thr Cys Leu Val Lys Gly Phe Tyr Pro Ser Asp Ile Ala
                165                 170                 175

Val Glu Trp Glu Ser Ser Gly Gln Pro Glu Asn Asn Tyr Asn Thr Thr
                180                 185                 190

Pro Pro Met Leu Asp Ser Asp Gly Ser Phe Phe Leu Tyr Ser Lys Leu
                195                 200                 205

Thr Val Asp Lys Ser Arg Trp Gln Gln Gly Asn Ile Phe Ser Cys Ser
                210                 215                 220

Val Met His Glu Ala Leu His Asn Arg Phe Thr Gln Lys Ser Leu Ser
225                 230                 235                 240

Leu Ser Pro Gly Lys
                245

<210> SEQ ID NO 44
<211> LENGTH: 330
<212> TYPE: PRT
<213> ORGANISM: Artificial Sequence
<220> FEATURE:
<223> OTHER INFORMATION: V-IGG3-D

<400> SEQUENCE: 44

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Gly Asp Thr Thr His Thr Cys Pro Arg Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Gln Phe Lys Trp
145                 150                 155                 160

Tyr Val Asp Gly Val Glu Val His Asn Ala Lys Thr Lys Pro Arg Glu
                165                 170                 175

Glu Gln Tyr Asn Ser Thr Phe Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Thr Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Ser Gly Gln Pro Glu Asn
```

```
                    260                 265                 270
Asn Tyr Asn Thr Thr Pro Pro Met Leu Asp Ser Asp Gly Ser Phe Phe
            275                 280                 285

Leu Tyr Ser Arg Leu Thr Val Asp Lys Ser Arg Trp Gln Gln Gly Asn
            290                 295                 300

Ile Phe Ser Cys Ser Val Met His Glu Ala Leu His Asn Arg Phe Thr
305                 310                 315                 320

Gln Lys Ser Leu Ser Leu Ser Pro Gly Lys
            325                 330

<210> SEQ ID NO 45
<211> LENGTH: 245
<212> TYPE: PRT
<213> ORGANISM: Artificial Sequence
<220> FEATURE:
<223> OTHER INFORMATION: V-IGG3-D-Fc

<400> SEQUENCE: 45

Gly Gly Gly Gly Ser Gly Gly Gly Ser Gly Gly Gly Gly Ser Lys
1               5                   10                  15

Thr Gly Asp Thr Thr His Thr Cys Pro Arg Cys Pro Ala Pro Glu Leu
            20                  25                  30

Leu Gly Gly Pro Ser Val Phe Leu Phe Pro Pro Lys Pro Lys Asp Thr
            35                  40                  45

Leu Met Ile Ser Arg Thr Pro Glu Val Thr Cys Val Val Asp Val
50                  55                  60

Ser His Glu Asp Pro Glu Val Gln Phe Lys Trp Tyr Val Asp Gly Val
65                  70                  75                  80

Glu Val His Asn Ala Lys Thr Lys Pro Arg Glu Glu Gln Tyr Asn Ser
            85                  90                  95

Thr Phe Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
            115                 120                 125

Pro Ile Glu Lys Thr Ile Ser Lys Thr Lys Gly Gln Pro Arg Glu Pro
            130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
            165                 170                 175

Val Glu Trp Glu Ser Ser Gly Gln Pro Glu Asn Asn Tyr Asn Thr Thr
            180                 185                 190

Pro Pro Met Leu Asp Ser Asp Gly Ser Phe Phe Leu Tyr Ser Arg Leu
            195                 200                 205

Thr Val Asp Lys Ser Arg Trp Gln Gln Gly Asn Ile Phe Ser Cys Ser
            210                 215                 220

Val Met His Glu Ala Leu His Asn Arg Phe Thr Gln Lys Ser Leu Ser
225                 230                 235                 240

Leu Ser Pro Gly Lys
            245

<210> SEQ ID NO 46
<211> LENGTH: 330
<212> TYPE: PRT
<213> ORGANISM: Artificial Sequence
<220> FEATURE:
<223> OTHER INFORMATION: V-IGG3-E
```

<400> SEQUENCE: 46

```
Ala Ser Thr Lys Gly Pro Ser Val Phe Pro Leu Ala Pro Cys Ser Arg
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Thr Cys Asn Val Asn His Lys Pro Ser Asn Thr Lys Val Asp Lys
                85                  90                  95
Arg Val Glu Leu Lys Thr Gly Asp Thr Thr His Thr Cys Pro Arg Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Gln Phe Lys Trp
145                 150                 155                 160
Tyr Val Asp Gly Val Glu Val His Asn Ala Lys Thr Lys Pro Arg Glu
                165                 170                 175
Glu Gln Tyr Asn Ser Thr Phe Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Thr Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Ser Gly Gln Pro Glu Asn
            260                 265                 270
Asn Tyr Asn Thr Thr Pro Pro Met Leu Asp Ser Asp Gly Ser Phe Leu
        275                 280                 285
Leu Tyr Ser Lys Leu Thr Val Asp Lys Ser Arg Trp Gln Gln Gly Asn
    290                 295                 300
Ile Phe Ser Cys Ser Val Met His Glu Ala Leu His Asn Arg Phe Thr
305                 310                 315                 320
Gln Lys Ser Leu Ser Leu Ser Pro Gly Lys
                325                 330
```

<210> SEQ ID NO 47
<211> LENGTH: 245
<212> TYPE: PRT
<213> ORGANISM: Artificial Sequence
<220> FEATURE:
<223> OTHER INFORMATION: V-IGG3-E-Fc

<400> SEQUENCE: 47

```
Gly Gly Gly Gly Ser Gly Gly Gly Ser Gly Gly Gly Gly Ser Lys
1               5                   10                  15
```

```
Thr Gly Asp Thr Thr His Thr Cys Pro Arg Cys Pro Ala Pro Glu Leu
                20                  25                  30

Leu Gly Gly Pro Ser Val Phe Leu Phe Pro Pro Lys Pro Lys Asp Thr
            35                  40                  45

Leu Met Ile Ser Arg Thr Pro Glu Val Thr Cys Val Val Val Asp Val
 50                  55                  60

Ser His Glu Asp Pro Glu Val Gln Phe Lys Trp Tyr Val Asp Gly Val
 65                  70                  75                  80

Glu Val His Asn Ala Lys Thr Lys Pro Arg Glu Glu Gln Tyr Asn Ser
                85                  90                  95

Thr Phe Arg Val Val Ser Val Leu Thr Val Leu His Gln Asp Trp Leu
                100                 105                 110

Asn Gly Lys Glu Tyr Lys Cys Lys Val Ser Asn Lys Ala Leu Pro Ala
            115                 120                 125

Pro Ile Glu Lys Thr Ile Ser Lys Thr Lys Gly Gln Pro Arg Glu Pro
            130                 135                 140

Gln Val Tyr Thr Leu Pro Pro Ser Arg Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Ser Gly Gln Pro Glu Asn Asn Tyr Asn Thr Thr
                180                 185                 190

Pro Pro Met Leu Asp Ser Asp Gly Ser Phe Leu Leu Tyr Ser Lys Leu
            195                 200                 205

Thr Val Asp Lys Ser Arg Trp Gln Gln Gly Asn Ile Phe Ser Cys Ser
210                 215                 220

Val Met His Glu Ala Leu His Asn Arg Phe Thr Gln Lys Ser Leu Ser
225                 230                 235                 240

Leu Ser Pro Gly Lys
                245

<210> SEQ ID NO 48
<211> LENGTH: 5
<212> TYPE: PRT
<213> ORGANISM: Artificial Sequence
<220> FEATURE:
<223> OTHER INFORMATION: Fc heterodimerization

<400> SEQUENCE: 48

Phe Leu Tyr Ser Lys
1               5

<210> SEQ ID NO 49
<211> LENGTH: 5
<212> TYPE: PRT
<213> ORGANISM: Artificial Sequence
<220> FEATURE:
<223> OTHER INFORMATION: Fc heterodimerization

<400> SEQUENCE: 49

Phe Leu Tyr Ser Arg
1               5

<210> SEQ ID NO 50
<211> LENGTH: 5
<212> TYPE: PRT
<213> ORGANISM: Artificial Sequence
<220> FEATURE:
<223> OTHER INFORMATION: Fc heterodimerization
```

```
<400> SEQUENCE: 50

Leu Leu Tyr Ser Lys
1               5

<210> SEQ ID NO 51
<211> LENGTH: 107
<212> TYPE: PRT
<213> ORGANISM: Artificial Sequence
<220> FEATURE:
<223> OTHER INFORMATION: IGKC HUMAN Immunoglobulin kappa constant

<400> SEQUENCE: 51

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 52
<211> LENGTH: 106
<212> TYPE: PRT
<213> ORGANISM: Artificial Sequence
<220> FEATURE:
<223> OTHER INFORMATION: IGLC1 HUMAN Immunoglobulin lambda constant 1

<400> SEQUENCE: 52

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 53
<211> LENGTH: 106
<212> TYPE: PRT
<213> ORGANISM: Artificial Sequence
<220> FEATURE:
<223> OTHER INFORMATION: IGLC2 HUMAN Immunoglobulin lambda constant 2

<400> SEQUENCE: 53

Gly Gln Pro Lys Ala Ala Pro Ser Val Thr Leu Phe Pro Pro Ser Ser
1               5                   10                  15
```

```
Glu Leu Gln Ala Asn Lys Ala Thr Leu Val Cys Leu Ile Ser Asp
         20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 54
<211> LENGTH: 5
<212> TYPE: PRT
<213> ORGANISM: Artificial Sequence
<220> FEATURE:
<223> OTHER INFORMATION: CD3 VL CDR1

<400> SEQUENCE: 54

Ser Ser Val Ser Tyr
1               5

<210> SEQ ID NO 55
<211> LENGTH: 3
<212> TYPE: PRT
<213> ORGANISM: Artificial Sequence
<220> FEATURE:
<223> OTHER INFORMATION: CD3 VL CDR2

<400> SEQUENCE: 55

Asp Thr Ser
1

<210> SEQ ID NO 56
<211> LENGTH: 9
<212> TYPE: PRT
<213> ORGANISM: Artificial Sequence
<220> FEATURE:
<223> OTHER INFORMATION: CD3 VL CDR3

<400> SEQUENCE: 56

Gln Gln Trp Ser Ser Asn Pro Phe Thr
1               5

<210> SEQ ID NO 57
<211> LENGTH: 8
<212> TYPE: PRT
<213> ORGANISM: Artificial Sequence
<220> FEATURE:
<223> OTHER INFORMATION: CD3 VH CDR1

<400> SEQUENCE: 57

Gly Tyr Thr Phe Thr Arg Tyr Thr
1               5

<210> SEQ ID NO 58
<211> LENGTH: 8
<212> TYPE: PRT
<213> ORGANISM: Artificial Sequence
<220> FEATURE:
<223> OTHER INFORMATION: CD3 VH CDR2
```

<400> SEQUENCE: 58

Ile Asn Pro Ser Arg Gly Tyr Thr
1               5

<210> SEQ ID NO 59
<211> LENGTH: 12
<212> TYPE: PRT
<213> ORGANISM: Artificial Sequence
<220> FEATURE:
<223> OTHER INFORMATION: CD3 VH CDR3

<400> SEQUENCE: 59

Ala Arg Tyr Tyr Asp Asp His Tyr Cys Leu Asp Tyr
1               5                   10

<210> SEQ ID NO 60
<211> LENGTH: 103
<212> TYPE: PRT
<213> ORGANISM: Artificial Sequence
<220> FEATURE:
<223> OTHER INFORMATION: IgG1-CH1

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 61
<211> LENGTH: 101
<212> TYPE: PRT
<213> ORGANISM: Artificial Sequence
<220> FEATURE:
<223> OTHER INFORMATION: IgG2-CH1

<400> SEQUENCE: 61

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys
            100

```
<210> SEQ ID NO 62
<211> LENGTH: 101
<212> TYPE: PRT
<213> ORGANISM: Artificial Sequence
<220> FEATURE:
<223> OTHER INFORMATION: IgG3-CH1

<400> SEQUENCE: 62

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys
            100

<210> SEQ ID NO 63
<211> LENGTH: 101
<212> TYPE: PRT
<213> ORGANISM: Artificial Sequence
<220> FEATURE:
<223> OTHER INFORMATION: IgG4-CH1

<400> SEQUENCE: 63

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys
            100

<210> SEQ ID NO 64
<211> LENGTH: 453
<212> TYPE: PRT
<213> ORGANISM: Artificial Sequence
<220> FEATURE:
<223> OTHER INFORMATION: human IgM constant region

<400> SEQUENCE: 64

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30
```

```
Phe Leu Pro Asp Ser Ile Thr Phe Ser Trp Lys Tyr Lys Asn Asn Ser
             35                  40                  45

Asp Ile Ser Ser Thr Arg Gly Phe Pro Ser Val Leu Arg Gly Gly Lys
 50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                 85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
            115                 120                 125

Lys Ser Lys Leu Ile Cys Gln Ala Thr Gly Phe Ser Pro Arg Gln Ile
            130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
            195                 200                 205

Asn Ala Ser Ser Met Cys Val Pro Asp Gln Asp Thr Ala Ile Arg Val
            210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
            275                 280                 285

Ser Ile Cys Glu Asp Asp Trp Asn Ser Gly Glu Arg Phe Thr Cys Thr
            290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
            370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Val Ala
                405                 410                 415

His Glu Ala Leu Pro Asn Arg Val Thr Glu Arg Thr Val Asp Lys Ser
            420                 425                 430

Thr Gly Lys Pro Thr Leu Tyr Asn Val Ser Leu Val Met Ser Asp Thr
            435                 440                 445

Ala Gly Thr Cys Tyr
```

<210> SEQ ID NO 65
<211> LENGTH: 349
<212> TYPE: PRT
<213> ORGANISM: Artificial Sequence
<220> FEATURE:
<223> OTHER INFORMATION: V-IGM

<400> SEQUENCE: 65

```
Val Ile Ala Glu Leu Pro Pro Lys Val Ser Val Phe Val Pro Pro Arg
1               5                   10                  15

Asp Gly Phe Phe Gly Asn Pro Arg Lys Ser Lys Leu Ile Cys Gln Ala
            20                  25                  30

Thr Gly Phe Ser Pro Arg Gln Ile Gln Val Ser Trp Leu Arg Glu Gly
        35                  40                  45

Lys Gln Val Gly Ser Gly Val Thr Thr Asp Gln Val Gln Ala Glu Ala
    50                  55                  60

Lys Glu Ser Gly Pro Thr Thr Tyr Lys Val Thr Ser Thr Leu Thr Ile
65                  70                  75                  80

Lys Glu Ser Asp Trp Leu Gly Gln Ser Met Phe Thr Cys Arg Val Asp
                85                  90                  95

His Arg Gly Leu Thr Phe Gln Gln Asn Ala Ser Ser Met Cys Val Pro
            100                 105                 110

Asp Gln Asp Thr Ala Ile Arg Val Phe Ala Ile Pro Pro Ser Phe Ala
        115                 120                 125

Ser Ile Phe Leu Thr Lys Ser Thr Lys Leu Thr Cys Leu Val Thr Asp
    130                 135                 140

Leu Thr Thr Tyr Asp Ser Val Thr Ile Ser Trp Thr Arg Gln Asn Gly
145                 150                 155                 160

Glu Ala Val Lys Thr His Thr Asn Ile Ser Glu Ser His Pro Asn Ala
                165                 170                 175

Thr Phe Ser Ala Val Gly Glu Ala Ser Ile Cys Glu Asp Asp Trp Asn
            180                 185                 190

Ser Gly Glu Arg Phe Thr Cys Thr Val Thr His Thr Asp Leu Pro Ser
        195                 200                 205

Pro Leu Lys Gln Thr Ile Ser Arg Pro Lys Gly Val Ala Leu His Arg
    210                 215                 220

Pro Asp Val Tyr Leu Leu Pro Pro Ala Arg Glu Gln Leu Asn Leu Arg
225                 230                 235                 240

Glu Ser Ala Thr Ile Thr Cys Leu Val Thr Gly Phe Ser Pro Ala Asp
                245                 250                 255

Val Phe Val Gln Trp Met Gln Arg Gly Gln Pro Leu Ser Pro Glu Lys
            260                 265                 270

Tyr Val Thr Ser Ala Pro Met Pro Glu Pro Gln Ala Pro Gly Arg Tyr
        275                 280                 285

Phe Ala His Ser Ile Leu Thr Val Ser Glu Glu Trp Asn Thr Gly
        290                 295                 300

Glu Thr Tyr Thr Cys Val Val Ala His Glu Ala Leu Pro Asn Arg Val
305                 310                 315                 320

Thr Glu Arg Thr Val Asp Lys Ser Thr Gly Lys Pro Thr Leu Tyr Asn
                325                 330                 335

Val Ser Leu Val Met Ser Asp Thr Ala Gly Thr Cys Tyr
            340                 345
```

```
<210> SEQ ID NO 66
<211> LENGTH: 240
<212> TYPE: PRT
<213> ORGANISM: Artificial Sequence
<220> FEATURE:
<223> OTHER INFORMATION: V-IGG2-D-Fc

<400> SEQUENCE: 66

Gly Gly Gly Gly Ser Gly Gly Gly Ser Gly Gly Gly Ser Tyr
1               5                   10                  15

Gly Pro Pro Cys Pro Pro Cys Pro Ala Pro Ala Ala Gly Pro Ser
                20                  25                  30

Val Phe Leu Phe Pro Pro Lys Pro Lys Asp Thr Leu Met Ile Ser Arg
            35                  40                  45

Thr Pro Glu Val Thr Cys Val Val Asp Val Ser His Glu Asp Pro
        50                  55                  60

Glu Val Gln Phe Asn Trp Tyr Val Asp Gly Val Glu Val His Asn Ala
65                  70                  75                  80

Lys Thr Lys Pro Arg Glu Glu Gln Phe Asn Ser Thr Phe Arg Val Val
                85                  90                  95

Ser Val Leu Thr Val Val His Gln Asp Trp Leu Asn Gly Lys Glu Tyr
            100                 105                 110

Lys Cys Ala Val Ser Asn Lys Gly Leu Pro Ala Pro Ile Glu Lys Thr
        115                 120                 125

Ile Ser Lys Thr Lys Gly Gln Pro Arg Glu Pro Gln Val Tyr Thr Leu
130                 135                 140

Pro Pro Ser Arg Glu Glu Met Thr Lys Asn Gln Val Ser Leu Thr Cys
145                 150                 155                 160

Leu Val Lys Gly Phe Tyr Pro Ser Asp Ile Ser Val Glu Trp Glu Ser
                165                 170                 175

Asn Gly Gln Pro Glu Asn Asn Tyr Lys Thr Thr Pro Pro Met Leu Asp
            180                 185                 190

Ser Asp Gly Ser Phe Phe Leu Tyr Ser Arg Leu Thr Val Asp Lys Ser
        195                 200                 205

Arg Trp Gln Gln Gly Asn Val Phe Ser Cys Ser Val Met His Glu Ala
210                 215                 220

Leu His Asn His Tyr Thr Gln Lys Ser Leu Ser Leu Ser Pro Gly Lys
225                 230                 235                 240

<210> SEQ ID NO 67
<211> LENGTH: 240
<212> TYPE: PRT
<213> ORGANISM: Artificial Sequence
<220> FEATURE:
<223> OTHER INFORMATION: V-IGG2-E-Fc

<400> SEQUENCE: 67

Gly Gly Gly Gly Ser Gly Gly Gly Ser Gly Gly Gly Ser Tyr
1               5                   10                  15

Gly Pro Pro Cys Pro Pro Cys Pro Ala Pro Ala Ala Gly Pro Ser
                20                  25                  30

Val Phe Leu Phe Pro Pro Lys Pro Lys Asp Thr Leu Met Ile Ser Arg
            35                  40                  45

Thr Pro Glu Val Thr Cys Val Val Asp Val Ser His Glu Asp Pro
        50                  55                  60

Glu Val Gln Phe Asn Trp Tyr Val Asp Gly Val Glu Val His Asn Ala
65                  70                  75                  80
```

```
Lys Thr Lys Pro Arg Glu Glu Gln Phe Asn Ser Thr Phe Arg Val Val
                85                  90                  95

Ser Val Leu Thr Val Val His Gln Asp Trp Leu Asn Gly Lys Glu Tyr
            100                 105                 110

Lys Cys Ala Val Ser Asn Lys Gly Leu Pro Ala Pro Ile Glu Lys Thr
        115                 120                 125

Ile Ser Lys Thr Lys Gly Gln Pro Arg Glu Pro Gln Val Tyr Thr Leu
    130                 135                 140

Pro Pro Ser Arg Glu Glu Met Thr Lys Asn Gln Val Ser Leu Thr Cys
145                 150                 155                 160

Leu Val Lys Gly Phe Tyr Pro Ser Asp Ile Ser Val Glu Trp Glu Ser
                165                 170                 175

Asn Gly Gln Pro Glu Asn Asn Tyr Lys Thr Thr Pro Pro Met Leu Asp
            180                 185                 190

Ser Asp Gly Ser Phe Leu Leu Tyr Ser Lys Leu Thr Val Asp Lys Ser
        195                 200                 205

Arg Trp Gln Gln Gly Asn Val Phe Ser Cys Ser Val Met His Glu Ala
    210                 215                 220

Leu His Asn His Tyr Thr Gln Lys Ser Leu Ser Leu Ser Pro Gly Lys
225                 230                 235                 240

<210> SEQ ID NO 68
<211> LENGTH: 15
<212> TYPE: PRT
<213> ORGANISM: Artificial Sequence
<220> FEATURE:
<223> OTHER INFORMATION: IgG1-like hinge

<400> SEQUENCE: 68

Lys Thr Gly Asp Thr Thr His Thr Cys Pro Arg Cys Pro Ala Pro
1               5                   10                  15

<210> SEQ ID NO 69
<211> LENGTH: 5
<212> TYPE: PRT
<213> ORGANISM: Artificial Sequence
<220> FEATURE:
<223> OTHER INFORMATION: GGGGS linker

<400> SEQUENCE: 69

Gly Gly Gly Gly Ser
1               5

<210> SEQ ID NO 70
<211> LENGTH: 20
<212> TYPE: PRT
<213> ORGANISM: Artificial Sequence
<220> FEATURE:
<223> OTHER INFORMATION: (GGGGS)4 linker

<400> SEQUENCE: 70

Gly Gly Gly Gly Ser Gly Gly Gly Gly Ser Gly Gly Gly Gly Ser Gly
1               5                   10                  15

Gly Gly Gly Ser
            20

<210> SEQ ID NO 71
<211> LENGTH: 25
<212> TYPE: PRT
<213> ORGANISM: Artificial Sequence
<220> FEATURE:
<223> OTHER INFORMATION: (GGGGS)5 linker
```

<400> SEQUENCE: 71

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 72
<211> LENGTH: 30
<212> TYPE: PRT
<213> ORGANISM: Artificial Sequence
<220> FEATURE:
<223> OTHER INFORMATION: (GGGGS)6 linker

<400> SEQUENCE: 72

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 73
<211> LENGTH: 15
<212> TYPE: PRT
<213> ORGANISM: Artificial Sequence
<220> FEATURE:
<223> OTHER INFORMATION: IgG1 hinge region

<400> SEQUENCE: 73

Lys Ser Cys Asp Lys Thr His Thr Cys Pro Pro Cys Pro Ala Pro
1               5                   10                  15

<210> SEQ ID NO 74
<211> LENGTH: 12
<212> TYPE: PRT
<213> ORGANISM: Artificial Sequence
<220> FEATURE:
<223> OTHER INFORMATION: IgG2 hinge region

<400> SEQUENCE: 74

Lys Cys Cys Val Glu Cys Pro Pro Cys Pro Ala Pro
1               5                   10

<210> SEQ ID NO 75
<211> LENGTH: 13
<212> TYPE: PRT
<213> ORGANISM: Artificial Sequence
<220> FEATURE:
<223> OTHER INFORMATION: IgG4 hinge region

<400> SEQUENCE: 75

Ser Lys Tyr Gly Pro Pro Cys Pro Ser Cys Pro Ala Pro
1               5                   10

<210> SEQ ID NO 76
<211> LENGTH: 13
<212> TYPE: PRT
<213> ORGANISM: Artificial Sequence
<220> FEATURE:
<223> OTHER INFORMATION: V-IGG2, -A, -B hinge region

<400> SEQUENCE: 76

Lys Asp Lys Thr His Thr Cys Pro Pro Cys Pro Ala Pro
1               5                   10

<210> SEQ ID NO 77

```
<211> LENGTH: 12
<212> TYPE: PRT
<213> ORGANISM: Artificial Sequence
<220> FEATURE:
<223> OTHER INFORMATION: V-IGG2-C, -D, -E hinge region

<400> SEQUENCE: 77

Lys Tyr Gly Pro Pro Cys Pro Pro Cys Pro Ala Pro
1               5                   10

<210> SEQ ID NO 78
<211> LENGTH: 13
<212> TYPE: PRT
<213> ORGANISM: Artificial Sequence
<220> FEATURE:
<223> OTHER INFORMATION: V-IGG3, -A, -B hinge region

<400> SEQUENCE: 78

Ser Lys Tyr Gly Pro Pro Cys Pro Pro Cys Pro Ala Pro
1               5                   10

<210> SEQ ID NO 79
<211> LENGTH: 16
<212> TYPE: PRT
<213> ORGANISM: Artificial Sequence
<220> FEATURE:
<223> OTHER INFORMATION: V-IGG3-C, -D, -E hinge region

<400> SEQUENCE: 79

Leu Lys Thr Gly Asp Thr Thr His Thr Cys Pro Arg Cys Pro Ala Pro
1               5                   10                  15

<210> SEQ ID NO 80
<211> LENGTH: 13
<212> TYPE: PRT
<213> ORGANISM: Artificial Sequence
<220> FEATURE:
<223> OTHER INFORMATION: V-IGG4-A, -B hinge region

<400> SEQUENCE: 80

Ser Lys Tyr Gly Pro Pro Cys Pro Pro Cys Pro Ala Pro
1               5                   10

<210> SEQ ID NO 81
<211> LENGTH: 4
<212> TYPE: PRT
<213> ORGANISM: Artificial Sequence
<220> FEATURE:
<223> OTHER INFORMATION: Dec-RVKR-cmk

<400> SEQUENCE: 81

Arg Val Lys Arg
1
```